United States Patent
Coombe et al.

(10) Patent No.: US 9,964,543 B2
(45) Date of Patent: May 8, 2018

(54) SELECTION OF MEDICAMENTS THAT MODULATE THE FUNCTION AND ACTIVITY OF INTERLEUKIN 13

(71) Applicant: GLYCAN BIOSCIENCES LLC, Philadelphia, PA (US)

(72) Inventors: Deirdre Roma Coombe, Wembleys Down Western Australia (AU); Barbara Mulloy, South Mimms (GB)

(73) Assignee: GLYCAN BIOSCIENCES LLC, Philadelphia, PA (US)

( * ) Notice: Subject to any disclaimer, the term of this patent is extended or adjusted under 35 U.S.C. 154(b) by 716 days.

(21) Appl. No.: 13/921,143

(22) Filed: Jun. 18, 2013

(65) Prior Publication Data

US 2013/0281318 A1  Oct. 24, 2013

Related U.S. Application Data

(62) Division of application No. 12/809,968, filed as application No. PCT/AU2008/001871 on Dec. 19, 2008, now abandoned.

(30) Foreign Application Priority Data

Dec. 21, 2007 (AU) ................................ 2007907059

(51) Int. Cl.
| | |
|---|---|
| G01N 33/68 | (2006.01) |
| A61K 31/715 | (2006.01) |
| A61K 31/726 | (2006.01) |
| A61K 31/727 | (2006.01) |
| C40B 30/02 | (2006.01) |
| G06F 19/16 | (2011.01) |
| G06F 19/00 | (2018.01) |

(52) U.S. Cl.
CPC ............ *G01N 33/68* (2013.01); *A61K 31/715* (2013.01); *A61K 31/726* (2013.01); *A61K 31/727* (2013.01); *C40B 30/02* (2013.01); *G06F 19/16* (2013.01); *G06F 19/706* (2013.01); *Y02A 90/26* (2018.01)

(58) Field of Classification Search
None
See application file for complete search history.

(56) References Cited

U.S. PATENT DOCUMENTS

2006/0073148 A1* 4/2006 Tchistiakova ........ C07K 16/244
424/145.1

FOREIGN PATENT DOCUMENTS

WO  WO 2005/100374 A1  10/2005

OTHER PUBLICATIONS

Bowie et al. (Science, 1990, 247:1306-1310).*
Bork (Genome Research, 2000,10:398-400).*
Samsonov et al (J Comput Aided Mol Des (2011) 25:477-489).*
Agostino et al (Glycobiology vol. 24 No. 9 pp. 840-851, 2014).*
NCBI Reference Sequence: NP_002179.2 (downloaded from http://www.ncbi.nlm.nih.gov/protein/NP_002179.2 on Oct. 5, 2015).*
Yu et al (J Immunol Apr. 2007 178 (Meeting Abstract Supplement) S181).*
Budavari, S. et al. 1989 *The Merck Index* 11$^{th}$ ed. Rahway, NJ:Merck & Co., Inc. (See Chemical Abstracts Registry Nos. 37300-21-3 (Pentosan polysulfate) and 9005-49-6 (Heparin).
Eisenmesser, E.Z. et al. 2001 "Solution Structure of Interleukin-13 and insights into receptor engagement" *Journal of Molecular Biology* 310:231-241.
Guru, T. 1997 "Systems for identifying new drugs are often faulty" *Science* 278: 1041-1042.
Tamaoki, J. 2002 "Molecular Mechanism of Airway Mucus Hypersecretion in Allergic Airway Inflammation" *Japanese Journal of Pharmacology, The Japanese Pharmacological Society* vol. 88: p. 56P, abstract No. S39-1.
Webb, D.C. et al. 2001 "Expression of the Ym2 Lectin-binding Protein Is Dependent on Interleukin (IL)-4 and IL-13 Signal Transduction" *Journal of Biological Chemistry* 276: 41969-41976.
Zeng, D. et al. 2004 "Heparin attenuates symptoms and mast cell degranulation induced by AMP nasal provocation" *J Allergy and Clin Immunol* 114: 316-320.
Zuegg, J. et al. 2001 "Structural model of human IL-13 defines the spatial interactions with the IL-13R$\alpha$/IL-4R$\alpha$ receptor" *Immunology and Cell Biology* 79:332-339.

* cited by examiner

*Primary Examiner* — Brian Gangle
*Assistant Examiner* — Andrea K McCollum
(74) *Attorney, Agent, or Firm* — Knobbe, Martens, Olson & Bear, LLP

(57) ABSTRACT

Medicaments in the form of therapeutic molecules including inflammatory modulators are designed and selected. A target site is on Interleukin 13 (IL-13) in which a glycosaminoglycan (GAG) molecule or polyanionic glycoconjugate or anionic polysaccharide modulates IL-13 activity or function. The target site can include amino acids located in the AB loops and/or helix D of human IL-13 or its homolog or derivative. The IL-13 target site is used to design a medicament for modulating physiological processes. Therapeutic and prophylactic compositions can include the designed medicaments.

5 Claims, 8 Drawing Sheets

A

B

A

B

SELECTION OF MEDICAMENTS THAT MODULATE THE FUNCTION AND ACTIVITY OF INTERLEUKIN 13

FILING DATA

This application is a divisional of application Ser. No. 12/809,968, filed Sep. 22, 2010, which is a U.S. National Phase of International Application No. PCT/AU2008/001871, filed Dec. 19, 2008, which claims the benefit of Australian Application No. 2007907059, filed Dec. 21, 2007, all of which are hereby expressly incorporated by reference in their entireties.

FIELD

The present invention relates generally to the field of medicaments in the form of therapeutic molecules including inflammatory modulators and their design and selection. Therapeutic and prophylactic compositions comprising the medicaments are also contemplated.

BACKGROUND

Bibliographic details of the publications referred to by author in this specification are collected at the end of the description.

Reference to any prior art in this specification is not, and should not be taken as, an acknowledgment or any form of suggestion that this prior art forms part of the common general knowledge in any country.

The design and selection of therapeutic molecules having a high degree of target specificity is a major goal of pharmaco-mimetic research. With the rapid development of complex computational algorithms, in silico screening is now a reasonable approach to rational drug design. The difficulty, however, is the identification of not only target molecules but conformationally active pockets, clefts and sites on these molecules.

The identification of therapeutic molecules useful in inflammation is particularly important.

Inflammation is a complex multifactorial process, which includes the migration of neutrophils and monocytes from blood into tissue at inflammatory sites. This migration involves a series of sequential steps proceeding from tethering on endothelium under shear conditions in postcapillary venules (Smith, *Microcirculation* 7:385-394, 2000). The tethering event depends on adhesion molecules in the selectin family, E-selectin and P-selectin on the endothelium and L-selectin on the neutrophil as well as their respective ligands expressed on both cell types (Burns et al, *Physiol Rev* 83:309-336, 2003). The adhesion step primarily involves the interaction of integrins ($\alpha L\beta 2$, $\alpha M\beta 2$, $\alpha 4\beta 7$, $\alpha 4\beta 1$) with adhesion molecules of the Ig-superfamily (ICAM-1, ICAM-2, MadCAM and VCAM) (Fabbri et al, *Inflamm Res* 48:239-246, 1999). Whereas, the transendothelial cell migration step involves molecules expressed at the junctions between adjacent endothelial cells.

Chronic inflammatory diseases affecting the lung such as bronchial asthma, chronic obstructive pulmonary disease (COPD) and allergic rhinitis are particularly problematic which cause high levels of morbidity and mortality. Asthma is particularly prevalent and is often triggered by exposure to environmental stimuli such as allergens, pharmacological agents, infectious agents, airborne pollutants and irritants.

One cytokine associated with inflammatory lung conditions is interleukin-13 (IL-13). IL-13 is a 17 kDa glycoprotein which has been cloned from activated T-cells (Zurawski and dVries, *Immunol Today* 15:19-26, 1994). It is a member of the cytokine family characterized by a tertiary structure of four $\alpha$-helical bundles. The helices are defined as helix A through D. The turns in the helices are referred to as loops, i.e. AB, BC and CD loops. Other members of this family include IL-2, IL-3, IL-4, IL-5 and GM-CSF. It was originally described as a T cell-derived cytokine that inhibits inflammatory cytokine production, however numerous other functions are also attributable to IL-13. These include the regulation of gastrointestinal parasite expulsion, airway hyperresponsiveness (AHR), allergic inflammation, atopic dermatitis, chronic obstructive pulmonary disease (COPD), tissue eosinophilia, mastocytosis, IgE antibody production, goblet cell hyperplasia, tumor cell growth, intracellular parasitism, tissue remodeling and fibrosis (Wynn, *Annu. Rev. Immunol.* 21:425-56, 2003). The gene encoding human IL-13 is located on chromosome 5Q31, in the same 3000 kb cluster of genes that encodes IL-3, IL-4, IL-5, IL-9 and GM-CSF. The IL-13 gene is 12 kb upstream from the gene encoding IL-4 and lies in the same orientation, indicating that these genes arose by gene duplication during evolution (de Waal Malefyt and de Vries, *The Cytokine Handbook*, 3rd Edn. A. W. Thomson, Editor: 427-442, 1998). The IL-13 protein has only 25% homology with IL-4 but it does display some similarities of function due to the sharing of a receptor complex with IL-4.

The IL-13 receptor complex includes the IL-4 receptor (IL-4R$\alpha$) chain and two other IL-13 binding proteins, IL-13R$\alpha$1 and IL-13R$\alpha$2. Both IL-13R$\alpha$1 and IL-13 R$\alpha$2 bind IL-13 but only IL-13R$\alpha$1 interacts with IL-4 despite IL-13R$\alpha$2 sharing a 37% homology with IL-13R$\alpha$1 (Andrews et al, *J. Allergy Clin. Immunol* 120:91-97, 2007). IL-13R$\alpha$1 by itself binds IL-13 with low-moderate affinity (2-10 nM), but in the presence of the IL-4R$\alpha$ chain, it binds IL-13 with high affinity (kd ~300-400 $\mu$M). In contrast, IL-13 R$\alpha$2 binds IL-13 with high affinity (0.5-1.2 nM) affinity but it appears not to contribute to IL-13 signaling. It has been suggested that it acts as a decoy receptor. Thus, the heterodimeric complex formed by the IL-13R$\alpha$1 and IL-4R$\alpha$ chains constitutes the functional IL-13 receptor (Wills-Karp, *Immunol. Rev.* 202:175-190, 2004). There is a sequential binding sequence for this receptor complex where IL-13 first binds IL-13R$\alpha$1 and then recruits IL-4R$\alpha$ to form a high affinity binding site (Andrews et al, *J. Immunol.* 176:7456-7461, 2006). Heterodimerization of IL-13R causes activation of Janus kinases, TYK2 and JAK1, constitutively associated with IL-13R$\alpha$1 and IL-4R$\alpha$, respectively, followed by activation of the signal transducer and activator of transcription 6 (STAT6).

The IL-13R (IL-4R$\alpha$/IL-13R$\alpha$1) is expressed on hemopoietic and non-hemopoietic cells including B cells, monocytes/macrophages, dendritic cells, eosinophils, basophils, fibroblasts, endothelial cells, airway epithelial cells and airway smooth muscle cells. IL-13 R$\alpha$2 has been found on airway smooth muscle cells and airway epithelial cells. IL-13 R$\alpha$2 has been described as a decoy receptor and a fusion protein consisting of IL-13 R$\alpha$2 and the Fc portion of immunoglobulin is used as an inhibitor of IL-13 in vitro and in vivo. IL-4 can also use IL-13R (IL-4R$\alpha$/IL-13 R$\alpha$1) as well as another receptor consisting of IL-4R$\alpha$ and the common $\gamma$-chain of the IL-2 receptor. This overlap of receptors accounts for many of the functional similarities of IL-4 and IL-13 (Andrews et al, 2006 supra).

The sites on the IL-13 molecule recognized by each of the receptor chains differ. For example molecular modeling has suggested that the D-helix of IL-13 interacts with IL-13R$\alpha$1 whereas parts of the A and C-helices of IL-13 interact with the IL-4Rα chain of the IL-13R (Oshima and Puri, *J. Biol. Chem.* 276:15195-15191, 2001; Zuegg et al, *Immunol. Cell Biol.* 79:332-339, 2001). Mutations of glutamic acids at positions 12 and 15 in helix A and arginine and serine at positions 65 and 68 respectively in the C helix were found to be important for biological signaling through the IL-4Rα chain since their specific mutation resulted in loss and/or gain of function (Thompson and Debinski, *J. Biol. Chem.* 274:29944-29950, 1999). Indeed, mutation E12K produced a powerful antagonist that inhibits the activities of human IL-13 (Oshima and Puri, 2001 supra). Whereas amino acids in the D-helix have been described as important for binding to IL-13Rα1 and/or IL-13Rα2, these are H102, K104, K105, R108, E109 and R111 (Arima et al, *J. Biol. Chem.* 280:24915-24922, 2005; Madhankumar et al, *J. Biol. Chem.* 277:43194-43205, 2002). These data are supported by molecular modeling studies and the crystal structures of the signaling complex of IL-4Rα/IL-13/IL-13Rα1. Analyses of the crystal structure further suggest K104 and R108 on IL-13 are critically important for the interactions with IL-13Rα1 domain 3 (LaPorte et al, *Cell* 132:259-272, 2008). A stripe of amino acids on the A and D helices demarcates a hydrophobic canyon lined by the alkyl moieties of these amino acids. These side chains form clefts into which the receptors insert to contact the main chains of the cytokine A and D helices and of particular importance are the side chains of amino acids R108 and K104 on the D helix. Whereas it appears that R111 is important for binding to the soluble receptor IL-13Rα2 (Andrews et al, *J. Allergy Clin. Immunol.* 120:91-97, 2007). Domain 1 of IL-13Rα1 interacts with a hydrophobic saucer-shaped patch formed by the alkyl side chains of M33, D87, K89, T35 (LaPorte et al, 2008 supra).

The ability to modify IL-13 function would aid in the development of medicaments useful in the treatment of inflammatory conditions of the lung including asthma, anaphylaxis, emphysema and COPD, and other diseases to which IL-13 contributes including atopic dermatitis, fibrosis and various cancers, for example B chronic lymphocytic leukemia (B-CLL), Hodgkin's disease, where tumor growth/protection from apoptosis is promoted by IL-13, and other cancers in which IL-13 appears to antagonize tumor immunosurveillance (Wynn, 2003 supra). The link between IL-13 and fibrosis suggests that IL-13 antagonists may also be effective in a variety of situations where chronic exposure to IL-13 triggers excessive healing, tissue remodeling, or the formation of destructive tissue pathology in situations like idiopathic pulmonary fibrosis, chronic graft rejection, bleomycin-induced pulmonary fibrosis, progressive systemic sclerosis, radiation-induced pulmonary fibrosis, hepatic fibrosis and acute respiratory distress syndrome (ARDS).

Particular glycosaminoglycan (GAG) sequences can bind specifically and make unique interactions with a number of biomolecules including chemokines, growth factors, cytokines, proteins of the coagulation cascade (e.g. anti-thrombin III (AT-III)-pentasaccharide complex) and adhesion molecules. Very few GAG fragments, however, have been developed for therapeutic use, mostly because the synthesis of saccharide blocks is chemically challenging. The anti-thrombin (AT)-binding pentasaccharide ARIXTRA (Registered trade mark) [Sanofi] has been approved for use in thromboprophylaxis following orthopedic surgery and the GAG mimetic PI-88 (Progen) has progressed to clinical trials as an anti-cancer treatment. Other polyanionic polysaccharides (for example pentosan polysulfate) can also bind biomolecules including chemokines, growth factors, cytokines, proteins of the coagulation cascade (e.g. anti-thrombin III (AT-III)-pentasaccharide complex) and adhesion molecules in a manner resembling that of GAGs or GAG sequences.

There is a need to delineate the nature of the interactions of IL-13 with GAGs. This will enable development of small molecule selective modulators of GAG-IL-13 interactions. This includes blocking IL-13 signaling via its receptor (IL-13R) to thereby treat disease conditions that arise because of this signaling event.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

A structural model of the extracellular domains of IL-13, the location of sulfate binding regions and the modeling of the binding of various heparin and GAG fragments to IL-13 are provided herein. This has lead to the identification of the interactions and affinity of heparin and GAG fragments of various sizes to a particular binding site on IL-13. This in turn enables the determination of a molecular target for the design and selection of GAG-like molecules that are smaller than naturally occurring GAGs. It is proposed that these molecules that are GAG-like in nature but are smaller than naturally occurring GAGs (GAG mimetics/polyanionic glycoconjugates) have potential as therapeutic and prophylactic agents to modulate IL-13 activity and functions because they bind to IL-13 at a site that overlaps with the IL-13Rα1 and/or the IL-13Rα2 binding sites, thereby blocking IL-13 from interacting with these molecules and as a consequence blocking the formation of the IL-4Rα/IL-13 Rα1 complex which constitutes the functional IL-13 receptor. Hence, GAG mimetics/polyanionic glycoconjugates have a role as therapeutic and prophylactic agents in a range of disease processes such as inflammation, fibrosis, chronic graft rejection, cancer and stem cell differentiation and proliferation. In particular the allergic inflammatory diseases asthma, allergic rhinitis and atopic dermatitis or eczema and other inflammatory respiratory diseases like COPD and ARDS are likely to be positively affected by these molecules that are GAG-like in nature but are smaller than naturally occurring GAGs.

IL-13 comprises four helical bundles. Each helix is referred to as helix A, helix B, helix C and helix D, respectively. The turns in the helices are referred to as loops, hence AB, BC and CD loops. The amino acid numbering system used in this specification is that given in the human IL-13 monomer structure; 1ijz.pdb.

Accordingly, one aspect of the present invention is directed to a target site on IL-13 at which a GAG molecule or a polyanionic glycoconjugate modulates IL-13 activity or function, the target site comprising amino acids located on a region selected from the list consisting of the AB loop, helix D and a combination of the AB loop and helix D. The GAG/polyanionic glycoconjugate binding site overlaps the binding site on the D-helix of IL-13 for receptors, IL-13Rα1 and/or IL-13Rα2, thereby blocking IL-13 from interacting with these molecules and as a consequence blocking the formation of the IL-4Rα/IL-13 Rα1 complex which constitutes the functional IL-13 receptor.

A target site for the design and selection of IL-13 activity or function modifiers is further provided comprising a conformation of amino acid residues within a region selected from the list consisting of the AB loop, helix D and a combination of the AB loop and helix D.

Another aspect of the present invention provides a GAG or a polyanionic glycoconjugate binding site on IL-13 useful as a target site for the design and selection of IL-13 activity or function modifiers, the GAG binding site selected from the listing consisting of:
(i) a conformation of amino acid residues in the AB loop comprising amino acid residues Q22, Q24 and K25;
(ii) a conformation of amino acid residues on helix D selected from amino acid residues K97, D98, H102, K104, K105, R108, E109 and R111; and
(iii) a conformation of amino acid residues selected from amino acid residues Q22, Q24 and K25 in the AB loop and K97, D98, H102, K104, K105, R108, E109 and R111 in helix D.

These amino acids are in human IL-13 but the present invention extends to derivative IL-13 molecules including splice variants and polymorphic variants and the equivalent location in non-human IL-13 homologs.

Another aspect is directed to a GAG or a polyanionic glycoconjugate binding site on IL-13 useful as a target site for the design and selection of IL-13 activity or function modifiers, the GAG/polyanionic glycoconjugate binding site comprising amino acids Q22, Q24 and K25 in the AB loop and K97, D98, H102, K104, K105, R108, E109 and R111 in helix D.

A further aspect of the present invention is directed to an isolated agent which modifies IL-13 activity or function the agent capable of interacting with or antagonizing or agonizing binding of a GAG or a polyanionic glycoconjugate to a site on IL-13 selected from the list consisting of amino acid residues in the AB loop, amino acid residues in helix D and amino acid residues in the AB loop and helix D.

More particularly, the present invention provides an isolated agent, which interacts with or antagonizes or agonizes binding of a GAG or a polyanionic glycoconjugate to a site on IL-13 selected from the list consisting of:
(i) a conformation of amino acid residues in the AB loop comprising amino acid residues Q22, Q24 and K25 in human IL-13 or its equivalent in non-human IL-13;
(ii) a conformation of amino acid residues in helix D selected from amino acid residues K97, D98, H102, K104, K105, R108, E109 and R111 of human IL-13 or its equivalent in non-human IL-13; and
(iii) a conformation of amino acid residues selected from amino acid residues Q22, Q24 and K25 in the AB loop and K97, D98, H102, K104, K105, R108, E109 and R111 in helix D of human IL-13 or its equivalent in non-human IL-13.

Reference to "IL-13" includes mutants, derivatives, splice variants, polymorphism variants and the like. It particularly includes the naturally occurring human IL-13 variant IL-13R111Q, where an arginine at position 111 has been substituted with a glutamine. This variant is found in approximately 20% of the Caucasian population and a number of studies have shown strong associations between this IL-13 polymorphism and atopy and atopic diseases such as asthma, atopic dermatitis and allergic rhinitis (Andrews, 2007 supra).

The present invention also contemplates the use of a GAG or polyanionic glycoconjugate binding site on IL-13 in the design of a medicament for modulating physiological processes in a subject such as inflammatory processes.

Another aspect of the present invention is that heparin, a heparin oligosaccharide or a fraction or derivative of heparin acts as an antagonist of IL-13 because it binds to IL-13 at a site selected from the list consisting of:
(i) amino acid residues Q22, Q24 and K25 in the AB loop;
(ii) amino acid residues K97, D98, 11102, K104, K105, R108, E109 and R111 on helix D; and
(iii) amino acid residues Q22, Q24 and K25 in the AB loop and K97, D98, H102, K104, K105, R108, E109 and R111 on helix D.

Another aspect of the present invention is that a fraction or derivative of the sulfated xylan, pentosan polysulfate (PPS) acts as an antagonist of IL-13 because it binds to IL-13 at a site selected from the list consisting of:
(i) amino acid residues Q22, Q24 and K25 in the AB loop;
(ii) amino acid residues K97, D98, H102, K104, K105, R108, E109 and R111 on helix D; and
(iii) amino acid residues Q22, Q24 and K25 in the AB loop and K97, D98, H102, K104, K105, R108, E109 and R111 on helix D.

The present invention further contemplates sulfate binding motifs on the AB loop and/or helix D selected from the list consisting of:
(i) amino acid residues Q22, Q24 and K25 on the AB loop in human IL-13 or its equivalent in non-human IL-13;
(ii) amino acid residues K97, D98, H102, K104, K105, R108, E109 and R111 in helix D of human IL-13 or its equivalent in non-human IL-13; and
(iii) an amino acid residues Q22, Q24 and K25 in the AB loop and amino acid residues K97, D98, H102, K104, K105, R108, E109 and R111 on helix D of human IL-13 or its equivalent in non-human IL-13.

A further aspect provides the use of sulfate binding motifs in the AB loop and/or on helix D of IL-13 selected from the list consisting of:
(i) amino acid residues Q22, Q24 and K25 in the AB loop in human IL-13 or its equivalent in non-human IL-13;
(ii) amino acid residues K97, D98, H102, K104, K105, R108, E109 and R111 on helix D of human IL-13 or its equivalent in non-human IL-13; and
(iii) amino acid residues Q22, Q24 and K25 in the AB loop and K97, D98, H102, K104, K105, R108, E109 and R111 on helix D of human IL-13 or its equivalent in non-human IL-13;
in the manufacture of a medicament for modulating physiological processes including inflammatory processes.

The present invention also contemplates a method of treatment or prophylaxis in a subject the method comprising administering to a subject an IL-13 activity or function modifier which binds or interacts with a GAG or polyanionic glycoconjugate binding site on IL-13 selected from the list consisting of:
(i) amino acid residues Q22, Q24 and K25 in the AB loop;
(ii) amino acid residues K97, D98, H102, K104, K105, R108, E109 and R111 on helix D; and
(iii) amino acid residues Q22, Q24 and K25 in the AB loop and K97, D98, H102, K104, K105, R108, E109 and R111 on helix D.

Methods of design and selection of IL-13 activity and function modifiers including in silico screening and other computer-based methods are further contemplated herein.

Single and three letter abbreviations for amino acid residues used herein are defined in Table 1.

TABLE 1

Amino Acid Abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalamine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BRIEF DESCRIPTION OF THE FIGURES

Some figures contain color representations or entities. Color photographs are available from the Patentee upon request or from an appropriate Patent Office. A fee may be imposed if obtained from a Patent Office.

DETAILED DESCRIPTION

Figure 1:
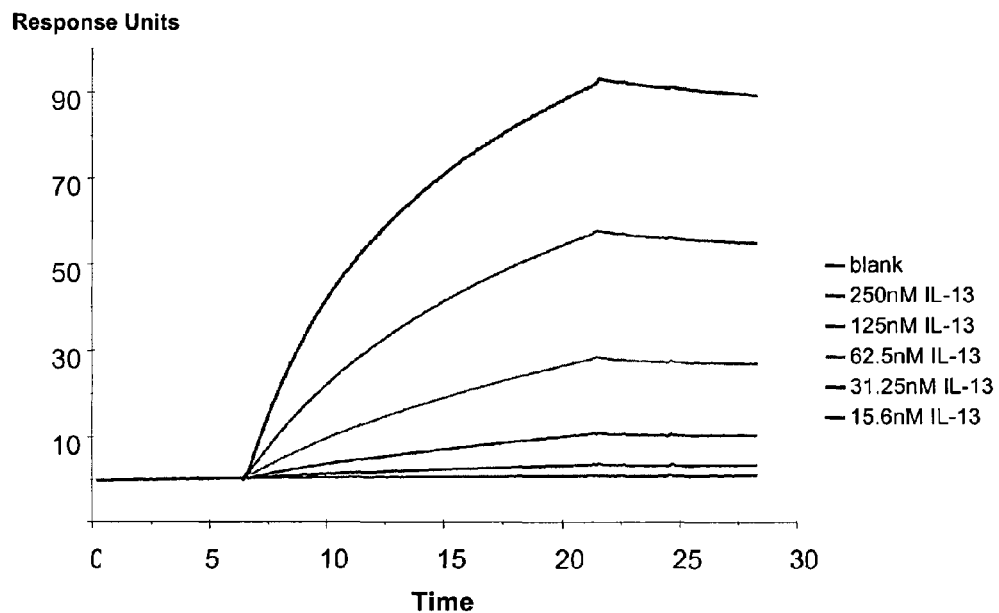
FIGS. 1A and B are a graphical representations showing (A) the binding of human IL-13 to heparin immobilized on a BIACORE sensor chip as determined by surface Plasmon resonance. IL-13 at the concentrations indicated was injected over heparin immobilized onto streptavidin sensor chips. The binding data were monitored during both the association and dissociation phases. (B) IL-13 binding to either the heparin coupled flow cell (fc2) or the blank flow cell (fc1). Plotted is the data for flow cell 2 minus that of flow cell 1 (fc2-1).
Figure 1:
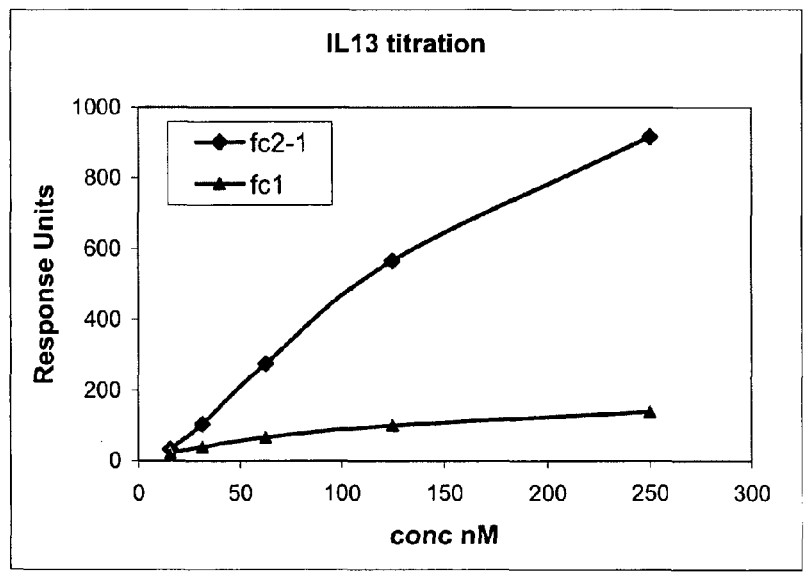

As used in the subject specification, the singular forms "a", "an" and "the" include plural aspects unless the context clearly dictates otherwise. Thus, for example, reference to "a target site" includes reference to a single target site or more than one target site; reference to "an amino acid" includes a single amino acid, as well as two or more active amino acids; reference to "the invention" includes reference to single or multiple aspects of an invention; and so forth.

The present invention provides target sites on IL-13 for the design and selection of specific antagonists and agonists of IL-13 function and activity. Such antagonists and agonists are proposed herein to be useful in modulating physiological processes including inflammation, cancer and stem cell differentiation and/or proliferation. All such conditions are conveniently encompassed herein by use of the term "physiological processes". Antagonists of IL-13 activity or function are particularly encompassed for use in the treatment of inflammation and in particular allergic inflammation.

Reference to "inflammation" or "inflammatory processes" include but are not limited to those diseases and disorders which result in a response of redness, swelling, pain, and a feeling of heat in certain areas that is meant to protect tissues affected by injury or disease. Inflammatory diseases which can be treated using the methods of the present invention, include, without being limited to, acne, allergic rhinitis, angina, arthritis, aspiration pneumonia, empyema, gastroenteritis, inflammation, intestinal flu, NEC, necrotizing enterocolitis, pelvic inflammatory disease, pharyngitis, PID, pleurisy, raw throat, redness, rubor, sore throat, stomach flu and urinary tract infections, chronic inflammatory demyelinating polyneuropathy, chronic inflammatory demyelinating polyradiculoneuropathy, chronic obstructive pulmonary disease (COPD), emphysema, asthma, acute respiratory distress syndrome (ARDS), Crohn's disease, ulcerative colitis, inflammatory bowel disease, systemic lupus erythematosus, rheumatoid arthritis, Alzheimer's disease, type I diabetes, gingivitis, eczema (atoptic dermatitis), psoriatic arthritis, tendinitis and multiple sclerosis. Allergic rhinitis, asthma, COPD, ARDSand atopic dermatitis are particular conditions contemplated herein.

In accordance with the present invention, amino acid residues in the AB loop, helix D or a combination of the AB loop and helix D of IL-13 define structural determinants for binding of GAG molecules or polyanionic glycoconjugates. This enables the development of GAG-like molecules and the design and selection of GAG-like molecules that are smaller than naturally occurring GAGs, which bind to IL-13 and modify its activity or function. Such molecules in turn are proposed to be useful drug candidates to modulate physiological events including inflammatory processes like asthma, anaphylaxis, emphysema, COPD atopic dermatitis and other diseases to which IL-13 contributes including fibrosis and various cancers, for example B chronic lymphocytic leukemia (B-CLL), Hodgkin's disease, where tumor growth/protection from apoptosis is promoted by IL-13, and other cancers in which IL-13 appears to antagonize tumor immunosurveillance. The link between IL-13 and fibrosis suggests that IL-13 antagonists may also be effective in a variety of situations where chronic exposure to IL-13 triggers excessive healing, tissue remodeling, or the formation of destructive tissue pathology in situations like idiopathic pulmonary fibrosis, ARDS, chronic graft rejection, bleomycin-induced pulmonary fibrosis, progressive systemic sclerosis, radiation-induced pulmonary fibrosis and hepatic fibrosis and to inhibit the growth and development of certain cancers.

Various approaches have been used to identify heparin/GAG binding sites on the surface of proteins on the basis of amino acid composition (Caldwell et al, *Int J Biochem Cell Biol* 28(2):203-216, 1996; Fromm et al, *Arch Biochem Biphys* 343(1):92-100, 1997), secondary structure (Hileman et al, *Bioessays* 20(2):156-167, 1998) spatial distribution of the basic amino acids (Margalit et al, *J Biol Chem* 268(26): 156-167, 1993) and the surface properties of proteins (Forster and Mulloy, *Biochem Soc Trans* 34(3):431-434, 2006). While consensus sequences such as XBBXBX and XBBBXXBX (where B is a basic residue and X can be any residue) have been suggested for heparin binding (Cardin and Weintraub, *Arteriosclerosis* 9(421-32, 1989), they are neither necessary nor sufficient to define a GAG binding site. GAG binding sites generally consist of a cluster of basic residues on the protein surface, but not necessarily in a continuous sequence. Moreover, even in a family of structurally related proteins, like the cytokine family characterized by a tertiary structure of four α-helical bundles, GAG binding sites are not necessarily located on the same helices. Thus, the GAG binding site on IL-4 involves the C-helix, the GAG binding site on IL-5 involves the C-helix and the β-pleated sheet consisting of the AB-loop of one monomer and the CD-loop of the other monomer (International Patent Publication No. WO 2005/100374 A1). This means the GAG binding site on a protein cannot be determined or predicted from the linear amino acid sequence nor from the tertiary structure of a protein.

Site directed mutagenesis involves the mutation of one or nucleotides within the DNA coding sequence of a protein, such that the expressed protein is altered in at least one amino acid. The mutant can then be screened in the heparin-binding assays described in this document for the effect on heparin binding. Mutants that affect heparin binding can be mapped on two or three dimensional protein models to ascertain their position in relation to each other, and to the protein as a whole. This technique can be used on any GAG-binding protein to gather information on any GAG-binding site on that protein [Tsiang, et al, *J. Biol. Chem.* 270: 16854-16863, 1995].

Accordingly, one aspect of the present invention is directed to a target site on IL-13 at which a GAG molecule or polyanionic glycoconjugate modulates IL-13 activity or function, the target site comprising amino acids located on a region selected from the list consisting of the AB loop and helix D.

Reference to a "target site" includes a conformational binding region comprising amino acid residues within IL-13 to which a GAG molecule or a polyanionic glycoconjugate interacts. It is a target site for a GAG molecule or for the design or selection of molecules which mimic or antagonize or promote GAG binding to IL-13 thereby increasing or decreasing IL-13 activity or function. These molecules are GAG-like but are smaller than naturally occurring GAGs. Hence, the target site is for the design and selection of IL-13 activity or function modifiers.

Accordingly, a target site for the design and selection of IL-13 activity or function modifiers is provided comprising a conformation of amino acid residues within the AB loop and/or helix D of IL-13.

The target sites in the AB loop and helix D can also be defined in terms of sulfate binding motifs. Hence, the present invention contemplates sulfate binding motifs in the AB loop and helix D of IL-13 selected from the list consisting of (i) amino acid residue Q22, Q24 and K25 of the AB loop in human IL-13 or its equivalent in non-human IL-13;

(ii) amino acid residues K97, D98, H102, K104, K105, R108, E109 and R111 in helix D of human IL-13 or its equivalent in non-human IL-13; and (iii) amino acid residue Q22, Q24 and K25 of the AB loop and amino acid residues K97, D98, H102, K104, K105, R108, E109 and R111 in helix D of human IL-13 or its equivalent in non-human IL-13.

As indicated above, the modifiers may be a GAG, a GAG composite molecule, a polyanionic glycoconjugate or any GAG-like molecule smaller than naturally occurring GAGs that may or may not comprise saccharide material.

As used herein the terms "GAG-composite" structures or molecules or "composite" structures or molecules are used interchangeably. In one embodiment, a GAG-composite structure comprises a saccharide structure that binds a target protein. In a particular aspect, the saccharide structure comprises two or more high charged (e.g. sulfated or phosphorylated) disaccharides or trisaccharides or tetrasaccharides or pentasaccharides or hexasaccharides or heptasaccharides or octasaccharides or any combination of these saccharides separated by a linker or linkers. The linker is not necessarily based on a GAG-like backbone. Rather, a linker such as an alkyl chain or a polyol structure, or polyethylene glycol is preferable. Further, it is not necessary for the highly charged saccharides to be based on GAG structures. Other sugars, such as a mannan, or chitosan, or xylan or dextran for example, may be used as the scaffold upon which to display the charged groups.

The term "modifiers" includes antagonists and agonists of IL-13 activity or function.

It is proposed herein that amino acid conformational sites on the AB loop and/or helix D are GAG binding sites.

Reference to a "conformation of amino acid residues" includes a pocket, cleft, face or region to which a GAG molecule or a polyanionic glycoconjugate binds on IL-13. It is proposed herein that in the AB loop amino acid residue Q22, Q24 and K25 and/or on helix D, amino acid residues K97, D98, H102, K104, K105, R108, E109 and R111 is/are involved in a GAG binding site of human IL-13 or its derivatives or polymorphic versions of human IL-13 in particular the IL-13 variant in which arginine at position 111 has been replaced by a glutamine and or the equivalent location in a non-human IL-13 molecule.

Reference herein to a "conformation" includes the binding pocket, cleft, face or region comprising sequential or non-sequential amino acid residues.

Hence, another aspect is directed to a GAG/polyanionic glycoconjugate binding site on IL-13 useful as a target site for the design and selection of IL-13 activity or function modifiers the GAG binding site selected from the listing consisting of:
(i) a conformation of amino acid residues in the AB loop comprising residue Q22, Q24 and K25;
(ii) a conformation of amino acid residues on helix D selected from amino acid residues K97, D98, H102, K104, K105, R108, E109 and R111; and;
(iii) a conformation of amino acid residues selected from amino acid residue Q22, Q24 and K25 in the AB loop and K97, D98, H102, K104, K105, R108, E109 and R111 in helix D.

The amino acid residue numbers given above are for human IL-13 using a single letter abbreviation for amino acid residues. The abbreviations for amino acid residues are defined in Table 1. However, the present invention extends to human homologs such as derivatives and splice variants an and in particular the IL-13 variant where arginine at position 111 is replaced with a glutamine as well as non-human homologs such as but not limited to, from mouse, rat, rabbit, guinea pig, pig (including domestic pig and wild boar), horse, sheep, cat, dog, canalid and cow IL-13 homologs. Natural variations between various IL-13 homologs may occur and hence amino acid residue numbers may change.

Hence, another aspect is directed to a GAG or a polyanionic glycoconjugate binding site on IL-13 useful as a target site for the design and selection of IL-13 activity or function modifiers the GAG binding site selected from the listing consisting of:

(i) a conformation of amino acid residues comprising amino acid residues Q22, Q24 and K25 in the AB loop of human IL-13 or its equivalent in a non-human IL-13;
(ii) a conformation of amino acid residues on helix D selected from amino acid residues K97, D98, H102, K104, K105, R108, E109 and R111 on human IL-13 or the equivalent in a non-human IL-13; and
(iii) a conformation of amino acid residue selected from amino acid residues Q22, Q24 and 1(25 in the AB loop of human IL-13 and K97, D98, H102, K104, K105, R108, E109 and R111 or helix D of human IL-13 or the equivalent in a non-human IL-13.

As indicated above, reference to "human IL-13" or any non-human IL-13 includes any derivatives or splice variants thereof.

It is clear that the IL-13 modifiers will have human and veterinary applications as well as animal husbandry applications such as in the horse, camel and dog racing industries and applications in wild animal control and protection. All such applications are encompassed by the present invention.

Particular amino acid residues forming the GAG binding site in the AB loop include Q22, Q24 and K25 and on helix D, K97, D98, H102, K104, K105, R108, E109 and R111 of human IL-13.

Accordingly, another aspect of the present invention contemplates a GAG or an polyanionic glycoconjugate binding site on IL-13 useful as a target for the design and selection of IL-13 activity or function modifiers; the GAG or polyanionic glycoconjugate binding site selected from the list consisting of:
(i) amino acid residues Q22, Q24 and K25 in the AB loop of human IL-13 or its equivalent in non-human IL-13 or a functional portion or region thereof;
(ii) amino acid residues K97, D98, H102, K104, K105, R108, E109 and R111 on helix D of human IL-13 or its equivalent in non-human IL-13 or a functional portion or region thereof; and
(iii) amino acid residues Q22, Q24 and K25 in the AB loop and K97, D98, H102, K104, K105, R108, E109 and R111 on helix D of human IL-13 or its equivalent in non-human IL-13.

Reference to a "functional portion or region" in relation to the GAG or polyanionic glycoconjugate binding site means that through natural or artificial selection or mutagenesis, one or more of the defined amino acid residues may be removed or modified without removing GAG or polyanionic glycoconjugate binding ability. Hence, the present invention is not necessarily limited to each group of amino acid residues in their entirety.

Another aspect of the present invention is directed to a GAG or polyanionic glycoconjugate binding site on IL-13 useful as a target for the design and selection of IL-13 activity or function modifiers the GAG binding site comprising Q22, Q24 and K25 in the AB loop and K97, D98, H102, K104, K105, R108, E109 and R111 on helix D human IL-13 or the equivalent in non-human IL-13.

The present invention further provides synthetic peptides comprising three or more amino acid residues comprising Q22, Q24 and K25 in the AB loop and/or comprising one or more of K97, D98, H102, K104, K105, R108, E109 and R111 on helix D of IL-13 or the equivalent in non-human IL-13 useful in screening assays or for generating antibodies.

As indicated above, the GAG or polyanionic glycoconjugate target sites in the AB loop and/or helix D can also be defined in terms of sulfate binding motifs. Hence, the present invention contemplates sulfate binding motifs in IL-13 selected from the list consisting of:
(i) amino acid residues Q22, Q24 and K25 in the AB loop of human IL-13;
(ii) amino acid residues K97, D98, H102, K104, K105, R108, E109 and R111 on helix D of human IL-13; and;
(iii) amino acid residue Q22, Q24 and K25 in the AB loop and K97, D98, H102, K104, K105, R108, E109 and R111 of helix D of human IL-13.

As indicated above, these sites extend to derivatives and splice variants of human IL-13 and the equivalent site in non-human IL-13 homologs.

The present invention extends to IL-13 activity or function modifiers. Such molecules may be antagonists or agonists of IL-13 or IL-13 interactions with a ligand such as a receptor or a receptor chain. All such modifiers may be referred to herein as agents, therapeutics, drugs, molecules, active agents or similar term. Whilst agonists and antagonists are contemplated herein, antagonists are particularly encompassed by the present invention.

Hence, the present invention is further directed to an isolated agent which modifies IL-13 activity or function the agent being capable of interacting with or antagonizing or agonizing binding of a GAG or a polyanionic glycoconjugate to a site on IL-13 comprising an amino acid in the AB loop and/or amino acids in helix D.

More particularly, the present invention provides an isolated agent which interacts with or antagonizes or agonizes binding of a GAG or a polyanionic glycoconjugate to a site on IL-13 comprising:

(i) a conformation of amino acid residues in the AB loop comprising amino acid residues Q22, Q24 and K25;

(ii) a conformation of amino acid residues on helix D comprising amino acid residues K97, D98, H102, K104, K105, R108, E109 and R111; and;

(iii) a conformation of amino acid residues comprising Q22, Q24 and K25 in the AB loop and K97, D98, H102, K104, K105, R108, E109 and R111 on helix D.

Yet another particular aspect of the present invention is directed to an isolated agent which interacts with or antagonizes or agonizes binding of a GAG to a site on IL-13 comprising Q22, Q24 and K25 in the AB loop and K97, D98, H102, K104, K105, R108, E109 and R111 on helix D of human IL-13 or the equivalent on a non-human IL-13 homolog.

The agents of the present invention may be identified, designed or selected by any number of means include in silico screening or modeling as well as x-ray crystallography, random screening, micro-array technology and the like.

Hence, in one example, a computer-based method of in silico screening is contemplated.

Screening or identifying a potential IL-13 modifier is suitably facilitated with the assistance of a computer programmed with software, which inter alia predicts binding of portions of a molecule to a GAG or a polyanionic glycoconjugate binding site on IL-13.

Thus, in another aspect, the present invention contemplates a computer program product for screening or designing an IL-13 modifier, the product comprising:

(a) code comprising coordinates or molecular shape defined by amino acid residue numbers Q22, Q24 and K25 in the AB loop and K97, D98, H102, K104, K105, R108, E109 and R111 on helix D of human IL-13 or the equivalent in non-human IL-13 or a functional portion or region thereof;

(b) code that screens known or theoretical ligands which might bind to the coordinates or molecule shape; and (c) a computer readable medium that stores the codes.

In a related aspect, the invention extends to a computer for screening or designing a IL-13 modifier, wherein the computer comprises:

(a) code comprising coordinates or molecular shape defined by amino acid residue numbers Q22, Q24 and K25 in the AB loop and K97, D98, H102, K104, K105, R108, E109 and R111 on helix D of human IL-13 or the equivalent in non-human IL-13 or a functional portion or region thereof;

(b) a working memory for storing instructions for processing the machine-readable data;

(c) a central-processing unit coupled to said working memory and to said machine-readable data storage medium to provide known or theoretical ligands which might bind to the coordinates or molecule step; and (d) an output hardware coupled to said central processing unit for receiving (a) and/or (b).

Another aspect provides a computer program product for screening or designing an IL-13 modifier, the product comprising:

(a) code comprising coordinates or molecular shape of:
  - (i) amino acid residues Q22, Q24 and K25 in the AB loop of human IL-13 or its equivalent;
  - (ii) amino acid residue numbers K97, D98, H102, K104, K105, R108, E109 and R111 or helix D of human IL-13 or their equivalent; and
  - (iii) amino acid residue numbers Q22, Q24 and K25 in the AB loop and K97, D98, H102, K104, K105, R108, E109 and R111 on helix D of human IL-13 or their equivalents.

(b) code that screens known or theoretical ligands which might bind to the coordinates or molecule shape; and (c) a computer readable medium that stores the codes.

A further aspect is directed to a computer for screening or designing an IL-13 modifier, wherein the computer comprises:

(a) code comprising coordinates or molecular shape of:
  - (i) amino acid residues Q22, Q24 and K25 in the AB loop of IL-13 or its equivalent;
  - (ii) amino acid residues K97, D98, H102, K104, K105, R108, E109 and R111 on helix D of human IL-13 or its equivalent; and
  - (iii) amino acid residue Q22, Q24 and K25 in the AB loop and K97, D98, H102, K104, K105, R108, E109 and R111 on helix D of human IL-13 or their equivalents, (b) a working memory for storing instructions for processing the machine-readable data;

(c) a central-processing unit coupled to said working memory and to the machine-readable data storage medium to provide known or theoretical ligands which might bind to the coordinates or molecule step; and (d) an output hardware coupled to said central processing unit for receiving (a) and/or (b).

In one version of these embodiments, a system including a computer comprising a central processing unit ("CPU"), a working memory which may be, e.g. RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to computer by input lines, may be implemented in a variety of ways. For example, machine-readable data of this invention may be inputted via the use of a modem or modems connected by a telephone line or dedicated data line. Alternatively or additionally, the input hardware may comprise CD. Alternatively, ROM drives or disk drives in conjunction with display terminal, keyboard may also be used as an input device.

Output hardware, coupled to computer by output lines, may similarly be implemented by conventional devices. By way of example, output hardware may include CRT display terminal for displaying a synthetic polynucleotide sequence or a synthetic polypeptide sequence as described herein. Output hardware might also include a printer, so that hard copy output may be produced, or a disk drive, to store system output for later use.

In operation, CPU coordinates the use of the various input and output devices coordinates data accesses from mass storage and accesses to and from working memory, and determines the sequence of data processing steps. A number of programs may be used to process the machine readable data of this invention.

The present invention further provides a magnetic data storage medium which can be encoded with machine readable data, or set of instructions, for designing a synthetic molecule of the invention, which can be carried out by a system such as described above. Medium can be a conventional floppy diskette or hard disk, having a suitable substrate, which may be conventional, and a suitable coating, which may be conventional, on one or both sides, containing magnetic domains whose polarity or orientation can be altered magnetically. Medium may also have an opening for receiving the spindle of a disk drive or other data storage device. The magnetic domains of coating of medium are polarized or oriented so as to encode in manner which may be conventional, machine readable data such as that described herein.

The present invention also provides an optically readable data storage medium which also can be encoded with such a machine-readable data, or set of instructions, for designing a synthetic molecule of the invention, which can be carried out by a system. Medium can be a conventional compact disk read only memory (CD-ROM) or a rewritable medium such as a magneto-optical disk, which is optically readable and magneto-optically writable. Medium preferably has a suitable substrate, which may be conventional, and a suitable coating, which may be conventional, usually of one side of substrate.

A particular form of in silico screening is described in Raghuraman et al, *J. Med. Chem.* 49:3553-3562, 2006. In essence docking methods are employed whereby various chemical groups are substituted in a pentasaccharide in place of sulfate groups. This form of docking is also referred to as combinatorial virtual screening.

The present invention provides, therefore, medicaments which modulate the level of IL-13 activity or function. Reference to "medicaments", "therapeutic molecules", "agents", "drugs", "components" and "pharmaceuticals" may also be used to describe molecules which interact IL-13 and modify the activity.

The present invention further contemplates methods of screening for drugs comprising, for example, contacting a candidate drug with a target site of IL-13 as identified herein. The screening procedure includes assay for the presence of a complex between the drug and a target site as well as screening for any change in function. Cell-based screening procedures are also contemplated.

One form of assay involves competitive binding assays. In such competitive binding assays, IL-13 is typically labeled. Free IL-13 is separated from any putative complex and the amount of free (i.e. uncomplexed) label is a measure of the binding of the agent being tested to IL-13. One may also measure the amount of bound, rather than free, IL-13.

It is also possible to label the putative agent rather than IL-13 and to measure the amount of agent binding to IL-13 in the presence and in the absence of the drug being tested. Such compounds may inhibit IL-13 or may protect IL-13 from being inhibited or, alternatively, may potentiate its inhibition.

A common cell based screening assay is to determine whether or not the agent being tested can inhibit cell proliferation that is induced by IL-13. TF-1 cells are an IL-13 responsive human cell line that is commonly used for this purpose. Generally IL-13 is preincubated with the agent under test and then the mixture is added to TF-1 cells and proliferation is allowed to occur for 48 hours before the cell number is determined. If the agent binds to IL-13 so as to stop IL-13 from interacting with its cell surface receptor chain complex, then the extent of cell proliferation in the presence of IL-13 mixed with the agent will be markedly lower than the extent of cell proliferation obtained when only the IL-13 is present. The same concentration of IL-13 is used in both situations.

Cell based screening assays also include examining whether or not the drug can modify the ability of leukocytes or leukocyte-like cell lines to traverse an endothelial cell layer grown in tissue culture. The endothelial cell layer is grown on the upper surface of a porous membrane supported on an insert added into the wells of a multi-welled plate. The leukocytes or leukocyte-like cell lines are added to the upper surface of the membrane in the presence of drug and the leukocytes are allowed to migrate across the endothelial cell layer and into the lower chamber. The extent of cell migration through the endothelial cell layer is monitored by means of a cell labeling dye, the level of dye uptake being quantified using a plate reader.

In another method, GAG molecules are modified to give a drug which can modulate the activity of IL-13. For example, sulfate groups on GAGs are modified by being substituted with various non-ionic moieties. If the sulfate group on the GAG chain is replaced with the appropriate moiety indicated for that amino acid with which it interacts then this modified GAG structure may still bind, but bind with different affinity or antagonize non-modified GAG binding.

Such a modified GAG may be a suitable therapeutic candidate or a mimetic thereof may be designed or selected. Hence, the present invention contemplates GAG molecules, modified GAGs, GAG-like molecules, polyanionic glycoconjugates and composite GAGs as potential therapeutic targets or as template molecules to which suitable mimetics or homologs or structural equivalents may be designed. A GAG-like molecule includes a GAG-like composite structure having GAG or GAG-like components and non-GAG components. The GAG or GAG-like molecules or GAG-like composite molecules may be derived from naturally occurring heparin-like GAGs or may be obtained by a process of chemical modification of a non-GAG polysaccharide or may be a composite structure which may only in part comprise a saccharide backbone.

These GAG or GAG-like oligosaccharides or GAG-like composite molecules are generally regarded as semi-synthetic and are generated from either large polymeric polysaccharides as starting materials or discrete terta-, penta-, hexa-, septa- or octasaccharide starting materials. The semi-synthetic oligosaccharides may have varying degrees of charged species, for example sulfates and/or phosphates. In addition, compounds may undergo a number of other modifications including modifications such as the addition of side branches and phosphorylation of the GAG oligosaccharides.

A library can also be made of the composite structures. In this case there will be differences in the length of the negatively charged units that resemble GAGs, differences in the length and composition of the linker that connects the negatively charged regions that resemble GAGs and differences in the angles and flexibility of the linker.

The linker structure of the GAG-like composite molecule is selected from, but not limited to the following list comprising peptide, polypeptide or protein, chemical moiety, metal complexing agent, saturated or unsaturated fatty acid, lipid, dendrimer, saccharide, polyol, dextran, polyethylene glycol and branched or unbranched, saturated or unsaturated hydrocarbon chain.

The GAG-like oligosaccharides or the oligosaccharides of the GAG-like composite molecule comprise saccharides selected from, but not limited to the following list consisting of glucuronic acid, iduronic acid, glucosamine, N-acetylglucosamine, galactosamine, mannose, mannan, dextran, glucose, galactose, fructose, sucrose, fucose, heptulose, pentose, xylose, arabinose, manuronic acid, anhydrogalactose and guluronic acid. The oligosaccharide may be obtained by a process of chemical modification comprising enzymatic or chemical digestion of a polysaccharide of populations of polysaccharides and a step selected from the list comprising deacetylation; sulfation; desulfation; phosphorylationa and attachment of side chains. The oligosaccharides may comprise a sulphated and/or phosphorylated form thereof and/or acetylated form thereof or contain alkyl ether derivatives comprising methyl, ethyl, propyl or butyl. The GAG molecules include heparin, heparan sulfate and pentosan polysulfate (PPS). Hence, heparin, heparan sulfate, PPS and fractions or derivatives thereof are contemplated herein to bind to IL-13 or to inhibit IL-13/IL-13R interaction.

Truncation of the polysaccharides into oligosaccharides can be achieved via a number of mechanisms. The methods employed to truncate the polysaccharide include enzymatic, chemical, thermal and ultrasonic protocols such as described by Alban and Franz, *Biomacromolecules* 2: 354, 2001.

The termini of the GAG-like oligosaccharides or the oligosaccharides of the GAG-like composite molecule comprises 4-deoxy-L-threo-hex-4-enopyranosyluronic acid. The GAG-like oligosaccharide or the oligosaccharides of the GAG-like composite molecule contains a terminal glucosamine which is modified as a result of nitrous acid treatment and is selected from the group consisting of 2,5-anhydro-D-mannitol and 2,5-anhydro-D-mannose.

The saccharide unit of the GAG-like oligosaccharides or the oligosaccharides of the GAG-like composite molecule has one or more mono-, di-, or tri-saccharide units appended to hydroxyl groups in the 6 position to give a branched structure.

The present invention is further directed to compositions such as pharmaceutical compositions comprising the IL-13 modifiers herein contemplated.

The terms "modifier", "compound", "active agent", "pharmacologically active agent", "medicament", "active" and "drug" are used interchangeably herein to refer to a molecule that induces a desired pharmacological and/or physiological effect and in particular antagonizes or agonizes IL-13 activity or function. The terms also encompass pharmaceutically acceptable and pharmacologically active ingredients of those active agents contemplated herein including but not limited to salts, esters, amides, prodrugs, active metabolites, analogs and the like. When the terms "modifier", "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc. The term "compound" is not to be construed as a chemical compound only but extends to peptides, polypeptides and proteins and chemical analogs thereof. The modifiers identified or screened in accordance with the present invention are proposed to be useful in modulating inflammatory processes including inhibiting inflammation, inhibiting fibrosis, inhibiting growth of cancer cells and promoting or inhibiting stem cell proliferation and/or differentiation. The modifier includes a GAG molecule, heparin and heparan sulfate as well as fractions or derivatives thereof, or GAG-like molecules like PPS or other anionic polysaccharides.

The compounds, therefore, have an effect on reducing or preventing or treating inflammatory conditions. Reference to a "compound", "active agent", "pharmacologically active agent", "medicament", "active" and "drug" includes combinations of two or more actives such as one or more inhibitors and/or potentiators of IL-13 function or activity. A "combination" also includes a two-part or more such as a multi-part pharmaceutical composition where the agents are provided separately and given or dispensed separately or admixed together prior to dispensation.

The terms "effective amount" and "therapeutically effective amount" of an agent as used herein mean a sufficient amount of the agent to provide the desired therapeutic or physiological effect. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The pharmaceutical forms suitable for injectable use include sterile aqueous solutions (where water soluble), sterile powders for the extemporaneous preparation of sterile injectable solutions and inhalable forms. Such forms are preferably stable under the conditions of manufacture and storage and are generally preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredients in the required amount in the appropriate solvent with the active ingredient and optionally other active ingredients as required, followed by sterilization or at least a process to reduce contaminating viruses, bacteria or other biological entities to acceptable levels for administration to a human or animal subject. In the case of sterile powders for the preparation of sterile injectable solutions, suitable methods of preparation include vacuum drying and the freeze-drying technique that yields a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per second, minute, hour, day, week, month or year.

The tablets, troches, pills and capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, anti-bacterial and anti-fungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

The composition may also be formulated for local or topical administration. Techniques formulation and administration may be found in "Remington's Pharmaceutical Sciences", Mack Publishing Co., Easton Pa., 16th edition, 1980, Ed. By Arthur Osol. Thus, for local or topical administration, the subject compositions may be formulated in any suitable manner, including, but not limited to, creams, gels, oils, ointments, solutions, suspensions, powders, mists or aerosols. For transmucosal administration, penetrants appropriate to the barrier to be permeated are used in the formulation. Such penetrants are generally known in the art and include, but are not restricted to, benzalkonium chloride, digitonin, dihydrocytochalasin B, and capric acid.

The compositions of the subject invention in the form of lotions, creams or gels may contain acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, buffering agents, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

In one particularly preferred embodiment, the present invention contemplates an inhalant pharmaceutical composition.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of an condition or disorder such as an inflammatory condition or disorder. Generally, such a condition or disorder is an inflammatory response or mediates or facilitates an inflammatory response or is a downstream product of an inflammatory response. Thus, for example, the present method of "treating" a patient with an inflammatory condition or with a propensity for one to develop encompasses both prevention of the condition, disease or disorder as well as treating the condition, disease or disorder.

"Patient" as used herein refers to an animal, particularly a mammal and more particularly human who can benefit from the pharmaceutical formulations and methods of the present invention. There is no limitation on the type of animal that could benefit from the presently described pharmaceutical formulations and methods. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an "animal" includes an avian species such as a poultry bird, an aviary bird or game bird.

Particular animals are humans or other primates, livestock animals, laboratory test animals, companion animals or captive wild animals. A human is the most preferred target.

Examples of laboratory test animals include mice, rats, rabbits, guinea pigs and hamsters. Rabbits and rodent animals, such as rats and mice, provide a convenient test system or animal model. Livestock animals include sheep, cows, pigs, goats, horses and donkeys. Non-mammalian animals such as avian species, zebrafish, amphibians (including cane toads) and Drosophila species such as Drosophila melanogaster are also contemplated. Instead of a live animal model, a test system may also comprise a tissue culture system.

The present invention also contemplates the use of a GAG or polyanionic glycoconjugate binding site on IL-13 in the manufacture of a medicament for modulating a physiological process such as inflammatory processes in a subject.

As indicated above, the GAG or polyanioinc glycoconjugate binding site is selected from the list consisting of an amino acid in the AB loop, an amino acid on helix D and amino acids in the AB loop and on helix D.

More particularly, the GAG binding site is selected from the list consisting of:

(i) a conformation of amino acid residues comprising amino acid residues Q22, Q24 and K25 in the AB loop on human IL-13 or its equivalent;

(ii) a conformation of amino acid residues comprising K97, D98, H102, K104, K105, R108, E109 and R111 on helix D of human IL-13 or their equivalents; and (iii) a conformation of amino acid residues comprising Q22, Q24 and K25 in the AB loop and K97, D98, H102, K104, K105, R108, E109 and R111 on helix D of human IL-13 or their equivalents.

The IL-13 activity or function modifiers are particularly useful in the treatment of a range of inflammatory conditions such as allergic rhinitis, chronic obstructive pulmonary disease (COPD), emphysema, asthma, Crohn's disease, ulcerative colitis, inflammatory bowel disease, systemic lupus erythematosus, rheumatoid arthritis, Alzheimer's disease, type I diabetes, gingivitis, eczema (atoptic dermatitis), psoriatic arthritis, tendinitis and multiple sclerosis. Asthma and allergic rhinitis are particular conditions encompassed herein. The IL-13 activity or function modifiers are also useful in the treatment of other diseases to which IL-13 contributes including fibrosis and various cancers, for example B chronic lymphocytic leukemia (B-CLL), Hodgkin's disease, where tumor growth/protection from apoptosis is promoted by IL-13, and other cancers in which IL-13 appears to antagonize tumor immunosurveillance (Wynn, 2003 supra). The link between IL-13 and fibrosis suggests that IL-13 antagonists may also be effective in a variety of situations where chronic exposure to IL-13 triggers excessive healing, tissue remodeling, or the formation of destructive tissue pathology in situations like idiopathic pulmonary fibrosis, chronic graft rejection, bleomycin-induced pulmonary fibrosis, progressive systemic sclerosis, radiation-induced pulmonary fibrosis and hepatic fibrosis.

Hence, the present invention also contemplates a method of treatment or prophylaxis of a physiological process including an inflammatory process in a subject the method comprising administering to a subject an IL-13 activity or function modifier which binds or interacts with a GAG binding site on IL-13 selected from the list consisting of the AB loop and helix D.

In a particular embodiment, the GAG or polyanionic glycoconjugate binding site is selected from the list consisting of:

(i) a conformation of amino acid residues comprising Q22, Q24 and K25 in the AB loop of human IL-13 or its equivalent;

(ii) a conformation of amino acid residues comprising K97, D98, H102, K104, K105, R108, E109 and R111 in helix D of human IL-13 or their equivalents;

(iii) a conformation of amino acid residues comprising Q22, Q24 and K25 in the AB loop and K97, D98, H102, K104, K105, R108, E109 and R111 on helix D of human IL-13 or their equivalents.

The present invention is further described by the following non-limiting Examples. In these Examples, methods described below are employed.

Homology Modeling of IL-13

Sequences of the human, mouse, rat and porcine IL-13, as well as various alternatively spliced isoforms, are retrieved from the SWISS-PROT protein sequence database (Boeckmann et al, *Nucleic Acids Research* 31:365-370, 2003). Multiple sequence alignment are performed with CLUSTALW (Thompson et al, *Nucleic Acids Research* 22:4673-4680, 1994) using BLOSUM (BLOcks of Amino Acid Substitution Matrix) matrices in order to quantify the sequence similarity between individual subunits of IL-13 in different species and in the different isoforms. Initially, a PSI-BLAST (Altschul et al, *Nucleic Acids Research* 25:3389-3402, 1997) search against the Protein Data Bank is performed in order to find sequences that were homologous with human IL-13, so that proteins of known structure are identified and used as a global template for standard homology modeling. Additionally, different sequence and secondary structure prediction algorithms (PredictProtein [Rost et al, *Nucleic Acid Research* 32:W321-326, 2004] and PSIPRED [Bryson et al, *Nucleic Acid Research* 33:W36-38, 2005]) are used to predict the residues comprising the different secondary structures. The AB loop and helix D sequences, as classified by SWISSPROT are submitted to the fold recognition services Phyre (Kelley et al, *J Mol Biol* 299(2):499-520, 2000) [a successor algorithm of 3D-PSSM] and CBS Meta Server (Douguet and Labesse, *Bioinformatics* 17:752-753, 2001). Alignments are performed of the AB loop and helix D region of IL-13 with crystal structures of known AB loop and helix D regions using LALIGN/PLALIGN (Pearson and Lipman, *PNAS* 85(8):2444-2448, 1988). This allows the inclusion of new structural information available from time to time in the subsequent stages of the modeling studies. The statistical significance of an alignment is computed by aligning the two sequences and then shuffling the second sequence between 200 and 1000 times using the PRSS module (Pearson 1988 supra).

Structure construction, assignment of disulfide bridges, optimization and visualization are carried out using the molecular modeling package DS Modeling 1.7 (Accelrys, Inc.) Loops are built using the loop modeling protocol implemented in MODELLER (Fiser et al, *Protein Sci* 9(9): 1753-1773, 2000; Sali and Blundell, *J Mol Biol* 234(3):779-815, 1993). Essential hydrogen and charges are added to the structure. The structural quality of the resultant protein structure is tested using PROCHECK (Laskowski et al, *Journal of Applied Crystallography* 26(2):283-291, 1993), Eva123D (Douguet and Labesse 2001 supra) and Verify3D (Douguet and Labesse 2001 supra). Electrostatis potential calculations are done using the DELPHI program (Gilson and Honig, *Nature* 330(6143):84-86, 1987) implemented in DS Modeling 1.7 (Accelrys, Inc.) using the atomic partial charges assigned by CHARM with a protein interior dielectric constant of 4, a solvent dielectric constant of 80 and an ionic strength of 0.145M.

Alternatively high-resolution solution structures of human IL-13 have been determined by multidimensional NMR and have been deposited in the RCSB Protein Data Bank, PDB ID: 1ijz or 1iko (Moy et al, *J. Mol. Biol.* 310:219-230, 2001) or PDB ID: 1GA3 (Eisenmesser, et al, *J. Mol. Biol.* 310:231-241, 2001). These structures can be used instead of the homology modeling approach. The PDB is surveyed for sulfate binding motifs using BLAST searches for short overlapping segments for AB loops and helix D domains.

PatchDock (Schneidman-Duhovny et al, *Nucleic Acids Res* 33:W363-367, 2005; Schneidman-Duhovny et al, *Proteins* 52(1):107-112, 2003) is used to dock heparin and other GAG fragments to the entire IL-13 model. PatchDock is a fast geometry-based molecular docking algorithm that works by optimizing shape complementarity (hence, it is not an energy grid-based method). No constraints are used to define the binding site in order to allow the program to explore the entire surface of IL-13 and find appropriate interaction regions using an RMSD clustering in order to reduce the number of potential binding modes (Schneidman-Duhovny et al 2005 supra).

Most three-dimensional X-ray structures of GAG-protein complexes determined so far involve relative small oligosaccharides (di- to hexasaccharides) of varying affinity for their protein targets. In order to determine the minimal length of the heparin fragments required for binding to the AB loop/helix D domains of IL-13, docking simulations are performed with di- and pentasaccharides. The structure of the heparin pentasaccharide can be obtained from the crystal structure of annexin A2 complexed with an unsaturated hexasaccharide in PDB code 2HYV. Since no electron density is observed for the sixth saccharide residue (Shao et al, *J Biol Chem* 281(42):31689-31695, 2006), the pentassacharide is extracted directly from the structure. The residue at the non-reducing end of the heparin pentasaccharide is modified from UA2S by the addition of a hydrogen to the double bond between C-4 and C-5 to create a 4-deoxy IdoA2S residue (4dIdoA2S). This modeled pentasaccharide consists of 4dIdoA2S (1→4)GlcNS6 S(1→4)IdoA2S (1→4) GlcNS6S (1→4)IdoA2S. The pyranose rings of the glucosamine residues adopt a $^4C_1$ chair conformation whereas iduronic acids can adopt either a $^1C_4$ chair or a $^2S_o$ skew-boat conformation.

The structure of the disaccharide (IdoA2S (1→4) GlcNS6S)can be extracted from the reported NMR structures of a heparin dodecassacharide fragment (PDB structure 1HPN) [Mulloy et al, *Biochem J*293(3):849-858, 1993].

Docking of the dermatan sulfate (DS) tetrasaccharide (PDB code 1HM2) and a pentasaccharide extracted from chondroitin-4-sulfate (CS, PDB code 1C4S) is also performed. There is no crystal structure available for the dermatan sulfate pentasaccharide. The modeled DS tetrasaccharide consisted of IdoA(1→3)GalNAc4S(1→4)IdoA (1→3)GalNAc4S and the modeled CS consisted of GlcA (1→3)GalNAc4S(1→4)GlcA(1→3)GalNAc4S(1→4)GlcA Hydrogen atoms are added to these oligosccharides and the resultant structures are energy minimized in order to optimize the orientation of rotatable groups. The surface area, atomic contact energy and the binding score computed by PatchDock for the heparin pentasaccharide are extracted.

Further docking simulations are carried out using the program AutoDock 3.0 (Morris et al, *Journal of Computational Chemistry* 19(14):1639-1662, 1998). This program allows for flexibility in the ligand structure but uses a rigid body approximation for the protein receptor in order to speed up the calculation. AutoDock Tools (ADT) (Sanner and Python, *J Mol Graph Model* 17(1):57-61, 1999) are used to prepare the IL-13 molecule by adding appropriate hydrogens, partial atomic charges and salvation parameters.

Ligand rotatable bonds for all docked ligands are defined using the AutoTors module of AutoDock. The ligands were atom-type manually to ensure that they complied with the carbohydrate forcefield in AMBER (Weiner et al, *J. Am. Chem. Soc.* 106(3):765-784, 1984). The ligands are energy minimized in order to optimize the orientation of its hydrogen atoms. A grid spacing of 0.37 Å and a distance-dependent dielectric constant of 4.0 (as defined by Mehler and Somajer, *Protein Eng* 4(8):903-910, 1991) are used for the binding energy calculations, covering the putative binding site surface. Using AutoDock's Lamarckian genetic algorithm, heparin fragments are subjected to search runs using a population of individuals. The grid box is defined with a constant grid spacing of 0.37 Å around each heparin fragment using the binding poses obtained from PatchDock with respect to the AB loop and helix D domains of IL-13.

Due to the flexibility and size of the di- and pentasaccharides of heparin, the number of energy evaluations and the size of the genetic population are optimized to ensure convergence of the calculated energies, starting with a minimum of $5\times10^6$ and a maximum of $50\times10^6$ energy evaluations, as reported for blind docking (Hetenyi and van der Spoel, *Protein Sci* 11(7):1729-1737, 2002). Cluster analysis is performed on the resulting binding poses using a root mean square deviation (RMSD) tolerance of 1.0 Å. Since AUTODOCK cannot handle more than 32 rotatable bonds, the docking of the heparin fragments is performed keeping the hydroxyl groups fixed. The lowest docking energy binding scores of the disaccharides with full rotational freedom of their hydroxyl groups are verified to be similar to those obtained with the hydroxyl groups kept fixed, confirming that the initial orientation of the hydroxyl groups is appropriate for interactions with IL-13.

Combinatorial virtual screening is conducted by any number of means including the method of Raghuraman et al, 2006 supra.

Hence, a combinatorial virtual screening approach is proposed herein for predicting high specificity heparin/heparan sulphate sequences using the AB loop and helix D domains of IL-13-heparin pentasaccharide. Heparan sulphate/heparin pentasaccharide is simulated keeping the inter-glycosidic bond angles constant at the mean of the known solution values, irrespective of their sequence. Molecular docking using genetic algorithm (GA) implemented in softwares such as AutoDock and GOLD with restrained inter-glycosidic torsions and intra-ring conformations, but flexible substituents at the 2-, 4-, and 6-positions. Cluster analysis is performed on the resulting binding poses using an RMSD tolerance of 2.5 Å from the reference pose (docked pentasaccharide 2HYV).

The pentasaccharide sequence 2HYV, or sequence ABCDE [IdoA2S(1→4)GlcNS6S(1→4)IdoA2S(1→4) GlcNS6S(1→4)IdoA2S], is docked to AB loop and helix D domains of IL-13 using AutoDock. The glucosamine residues are modelled in a $^4C_1$ chair conformation whereas the iduronic acid can exist either in the $^2S_O$ or $^1C_4$ conformations. The ligands are atom-typed manually to ensure that they complied with the carbohydrate forcefield in AMBER. In SYBYL, the atom type of sulfur and oxygen atoms in $SO_3$ groups is modified to $^2S_o$ and $^2O_{co}$, respectively, and the bond type between these atoms was modified to aromatic bond. Hydrogen atoms, absent in the PDB structure, are added in SYBYL, and the resultant structure is minimized to optimize geometry of hydrogen atoms only (no change in non-H atoms). A grid spacing of 0.37 Å and a distance-dependent dielectric constant of 4.0 (as defined by Mehler and Solmajer, 1991 supra) are used for the binding energy calculations, covering the putative binding site surface. Using AutoDock's Lamarckian genetic algorithm, heparin fragments are subjected to search runs using a population of individuals with a maximum of $50 \times 10^6$ energy evaluations.

Docking is driven by the AutoDock scoring function. This free energy estimate of binding and docking energy including clustering is used to rank the final docked solutions.

The natural pentasaccharide structure docked to the AB loop/Helix D of IL-13 can be used as a template for the generation of GAG mimetics. GAG mimetics can consist of structures in which the GAG backbone is retained but the sulfates are variously replaced with particular structural groups, these structural groups include, but are not limited to, hypoxanthine, phenyl, amide and uracil groups. For each of these GAG mimetics consisting of structural modifications to the natural pentasaccharide sequence, minimization is performed with constraints that retain the sugar conformations. Because IdoA residues in heparin can exist either in the $^2S_O$ or $^1C_4$ conformations, each IdoA residue should be modeled explicitly in these two different states. The docking of these sequences can be carried out according to the protocol described above for the natural pentasaccharide.

A combinatorial library of heparin pentasaccharides is generated for docking onto AB loop/helix D of IL-13. The library considers the conformational flexibility of IdoA residue domains through inclusion of both $^1C_4$ and $^2S_O$ conformations. Thus, the combinatorial library consists of possible combinations of unique heparin pentasaccharides built with the average backbone geometry (similar to the natural pentasaccharide) in an automated manner. In addition, GAG mimetics may be generated by using a different structural backbone to display the sulphate residues in a fashion so as to facilitate binding to the GAG-binding site on IL-13 (GAG-like oligosaccharides).

The GAG mimetic may also comprise a GAG-like-composite structure and be classified as a polyanionic glycoconjugate. In a particular aspect, the saccharide structure comprises two or more high charged (e.g. sulfated or phosphorylated) disaccharides or trisaccharides or tetrasaccharides or pentasaccharides or hexasaccharides or heptasaccharides or octasaccharides or any combination of these saccharides separated by a linker or linkers. The linker is not necessarily based on a GAG-like backbone. Rather, a linker such as an alkyl chain or a polyol structure, or polyethylene glycol is preferable. Further, it is not necessary for the highly charged saccharides to be based on GAG structures. The GAG-like oligosaccharides or the oligosaccharides of the GAG-like composite molecule may comprise saccharides selected from, but not limited to the following list consisting of glucuronic acid, iduronic acid, glucosamine, N-acetylglucosamine, galactosamine, mannose, mannan, dextran, glucose, galactose, fructose, sucrose, fucose, heptulose, pentose, xylose, arabinose, manuronic acid, anhydrogalactose and guluronic acid. The oligosaccharide may be obtained by a process of chemical modification comprising enzymatic or chemical digestion of a polysaccharide of populations of polysaccharides and a step selected from the list comprising deacetylation; sulfation; desulfation; phosphorylationa and attachment of side chains. The oligosaccharides may comprise a sulphated and/or phosphorylation form thereof and/or acetylated form thereof or contain alkyl ether derivatives comprising methyl, ethyl, propyl or butyl.

Truncation of the polysaccharides into oligosaccharides can be achieved via a number of mechanisms. The methods employed to truncate the polysaccharide include enzymatic, chemical, thermal and ultrasonic protocols such as described by Alban and Franz, *Biomacromolecules* 2: 354, 2001.

The termini of the GAG-like oligosaccharides or the oligosaccharides of the GAG-like composite molecule comprises 4-deoxy-L-threo-hex-4-enopyranosyluronic acid. The GAG-like oligosaccharide or the oligosaccharides of the GAG-like composite molecule contains a terminal glucosamine which is modified as a result of nitrous acid treatment and is selected from the group consisting of 2,5-anhydro-D-mannitol and 2,5-anhydro-D-mannose.

In an alternate embodiment of the present invention, GAG oligosaccharides are generated by the method comprising size fractionating a population of heparin or heparan sulfate molecules or other polymers such as K5 polysaccharide, chitin or chitosan to generate non-full length fraction which interact with a ligand. Heparin comprises mixtures of glucuronic and iduronic acids in some of the disaccharide units and varying degrees of sulfation. Fractionation may be by any convenient means such as by gel filtration column and is based on different length saccharide chains generally but not exclusively from a degree of polymerization (DP)4 to about a DP20 such as DP5, DP6, DP7, DP8, DP9, DP10, DP11, DP12, DP13, DP14, DP15, DP16, DP17, DP18 or DP19. Another form of separation is on the basis of extent of sulfation. The separation may also be based on a combination of these two parameters.

Another aspect of the present invention is the provision of novel phosphorylated GAG oligosaccharides. These molecules are generated by the inclusion of a phosphorylation step when generating the library of GAG oligosaccharides. This phosphorylation step and any associated desulfation steps that may be necessary, is performed on both the semi-synthetic oligosaccharides derived from polymers such as *E. coli* K5 polymer, chitin or chitosan, and oligosaccharides produced by fractionation of GAGs such as heparin or heparan sulfate.

The 6-O sulfate is the easiest O-sulfate to hydrolyse, giving a way to access free 6-OH. The free 6-OH is then phosphorylated to give the 6-O phosphate. The sulfate and phosphate esters have been shown to be equipotent in many compounds although in others phosphorylation changes the activity. It is also possible to N-phosphorylate the glucosamine residue.

The selective phosphorylation of a hydroxyl group is readily achieved using the phosphoramidate-oxidation method (Vieira de Almeida et al, *Tetrahedron* 55: 7251-7270, 1999; Dubreuil et al, *Tetrahedron* 55: 7573-7582, 1999 and references cited therein) This method has been widely employed for the formation of inositol phosphates, nucleotides and oligonucleotides. Alternatively, several other more rapid methods for the introduction of a phosphate group could be employed such as phosphoryl oxychloride in the presence of pyridine followed by aqueous hydrolysis. It may also be possible to enzymatically phosphorylate these oligosaccharides through the agency of a promiscuous hexose kinase enzyme.

The saccharide unit of the GAG-like oligosaccharides or the oligosaccharides of the GAG-like composite molecule has one or more mono-, di-, or tri-saccharide units appended to hydroxyl groups in the 6 position to give a branched structure.

Each oligosaccharide pool, as produced according to the methods described above, is then tested for its ability to interact or bind to IL-13 or IL-13R. This may be performed experimentally or in silico.

The heparan sulfate/heparin pentasaccharide combinatorial library is made for screening all possible sequences using GA iterations implemented in AutoDock as described above. Free energy and docking energy scoring functions (see Table 2) in AutoDock aids in identifying the most promising sequences that have a relatively high binding affinity. The second step can consist of clustering these sequences with respect to the top two ranked solutions within 2.5 Å RMSD as compared to the natural pentasaccharide.

TABLE 2

| Energy scouring functions | |
|---|---|
| Estimated Free Energy of Binding | (1) + (3) |
| Docked Energy | (1) + (2) |

(1) Final Intermolecular Energy in kcal/mol
(2) Final Internal Energy of Ligand in kcal/mol
(3) Torsional Free energy in kcal/mol The approach facilitates the extraction of a pharmacophore, the key interactions to identify individual GAG sequences or GAG mimetics with high specificity. Energy scoring functions combined with a map of RMSD of atoms compared to the natural pentasaccharide can be readily created from the combinatorial library screening experiments to identify GAG sequences or GAG mimetic sequences which can define the pharmacophore. Thus, this approach is also useful for designing therapeutically useful molecules.

The interaction with a ligand may be measured experimentally by any convenient means such as gel retardation, filter retardation, affinity co-electrophoresis, bioluminescent resonance energy transfer (BRET) assays, fluoresence resonance energy transfer (FRET) assays, fluorescence polarization (FP) assays, scintillation proximity assays or immobilization to biochips or other surfaces including those coupled with mass spectrometric detection.

The latter may be accomplished by first immobilizing the GAG oligosaccharide or heparin or GAG-like polyanionic polysaccharidea polyanionic glycoconjugate to a chip and then adding the IL-13 in the fluid phase. Alternatively, IL-13 may be immobilized to a chip and used to screen for the ability of a GAG oligosaccharide, or heparin, or GAG-like polyanionic polysaccharide or a polyanionic glycoconjugate to bind thereto.

Yet another alternative is to immobilize a GAG, such as heparin, to a solid support and then screen for the ability of a polyanionic glycoconjugate, GAG-likepolyanionic polysaccharide or a GAG oligosaccharide, produced according to the methods above, to inhibit binding of IL-13 to the immobilized heparin.

Accordingly, a particularly useful assay is to admix IL-13 and the polyanionic glycoconjugate or a GAG oligosaccharide or GAG-like polyanionic polysaccharide and screen for the ability for of the polyanionic glycoconjugate, GAG oligosaccharide or GAG-like polyanionic polysaccharide to inhibit binding of IL-13 to a GAG (e.g. heparin or heparan sulfate) bound to a chip.

A common cell based assay involves testing whether or not the polyanionic glycoconjugate or a GAG oligosaccharide or a GAG-like polyanionic polysaccharide can inhibit cell proliferation that is induced by IL-13. TF-1 cells are an IL-13 responsive human cell line that is commonly used. IL-13 is preincubated with the agent under test and then the mixture is added to TF-1 cells and proliferation is allowed to occur for 48 hours before the cell number is determined. If the agent binds to IL-13 so as to stop IL-13 from interacting with its cell surface receptor chain complex, then the extent of cell proliferation in the presence of IL-13 mixed with the agent will be markedly lower than the extent of cell proliferation obtained when only the IL-13 is present. The same concentration of IL-13 is used in both situations.

Example 1

Sequence and Structure in Heparin and Heparan Sulfate

The most intensively studied and best understood sequence of monosaccharide residues in heparin is an unusual pentasaccharide which is the minimum requirement for high affinity to antithrombin. It is this sequence which accounts for the high anticoagulant potency of heparin, and hence its use as an antithrombotic agent; the essential pentasaccharide has been prepared synthetically and is itself used as a drug (Petitou and van Boeckel, Angew. Chem. Int. Edit. 43:3118, 2004). When it became clear that heparin, as a model compound for heparan sulfate, was capable of physiologically important interactions with other classes of protein, such as the fibroblast growth factors (Mohammadi et al, Curr. Opin. Struct. Biol. 15:506, 2005), the example of the antithrombin-binding sequence led to a search for other, equally specific sequences in either heparin or heparan sulfate which would confer particular affinity for any given binding partner. This search for specificity of a high order has on the whole been unsuccessful, and a recent study of structures which are capable of potentiating fibroblast growth factor (FGF)-mediated cell growth has concluded that heparan sulfate fine structure may be less influential than has previously been supposed (Kreuger and Spillmann, J. Cell Biol 174:323, 2006).

Heparan sulfate is often represented, and imagined, in terms of sequences, rather than three-dimensional structures (Mulloy, Anais Acad. Bras. Cienc. 77:651, 2005). The crystal structure of FGF-1 (2axm.pdb) complexed with a heparin oligosaccharide (Stauber et al, Proc. Natl. Acad. Sci. USA 97:49, 2000) shows clearly that the pattern of sulfate groups interacting with the protein can be formed in two ways, involving clusters of sulfate and carboxylate substituents on either side of the polysaccharide chain. Two separate molecules of FGF-1, aligned in opposite directions along the heparin chain, each interact with a cluster of three sulfates, part of a second cluster, and the carboxylate between the two clusters. The charge-based interactions, between the acidic substituents on the polysaccharide and basic residues on the surface of the protein, usually dominate the interface, and the detailed nature of the sugar backbone carrying the substituents is much less important, so long as it presents the substituents in an appropriate three-dimensional pattern. This "pseudo-symmetry", in which the underlying asymmetry of the sugar backbone is hidden by the almost symmetrical arrangement of bulky and highly charged substituents, is a complicating factor in the interpretation of heparan sulfate sequence requirements for affinity with different proteins. Another such factor is the finding that, for most interactions between heparin and proteins, substitution with additional sulfate groups does not decrease affinity. Bearing in mind both factors together, a simplistic calculation indicates 31 different pentasaccharide sequences (starting and ending with glucosamine) which will contain a single FGF-1 binding motif Leaving the motif on one side of the molecule undisturbed, and assuming that any or all of the four remaining sulfated positions may or may not be occupied, 16 ($2^4$) different possible compounds can be defined. Repeating this exercise for the second side gives 31 possible sequences in all (not counting the fully sulfated compound twice). Such a sequence is more likely to occur in highly sulphated regions of the polysaccharide. Potentiation of growth factor activity is more complex than simple affinity for the growth factor itself, and it is clear that the requirements for functional interaction with the growth factor/receptor complex are not the same as for the growth factor alone (Ostrovsky et al, *J. Biol. Chem.* 277:2444, 2002); still, the search for a 3-D pattern is more likely to be successful than for a specific sequence.

Example 2

Drug Discovery Techniques

Molecular modeling techniques, in particular those in which a small molecule is docked into its binding site, are used in the design of new drugs.

A conventional application of theoretical techniques to the process of designing a new drug would be to take a particular protein, for example an enzyme, and to look at the detailed experimental structure of a complex between the protein and its ligand, for example a substrate or inhibitor. On the basis of the structural details of IL-13 and its binding site for GAGs, new compounds are proposed. The compounds are screened by molecular modeling, using the technique known as docking calculations, which explore many mutual orientations of protein and ligand to find out how best to accommodate the ligand in the binding site. Compounds with the best affinity for the protein produce theoretical complexes with favorably low interaction energies.

Example 3

BIACORE Screening Assay

The optical phenomenon of surface plasmon resonance is used to monitor physical interactions between molecules. Passing a solution of a potential protein ligand (e.g. IL-13) over a sensor surface to which a target (e.g. heparin) is coupled monitors the real-time binding of protein ligands to the immobilized target. Detection is achieved by measuring refractive index changes very close to the sensor surface. When the refractive index is altered, the angle at which plasmon resonance occurs changes and this change directly correlates with the amount of protein interacting with the surface. A BIACORE 2000 sensor chip is conveniently used. It is very sensitive and its microfiuidics ensures that only small amounts of material are required.

Biotinylated heparin is immobilized on the biosensor chip. Biotinylation occurs via amino groups, or reducing termini modified with ammonia by reductive amination, using sulfo-NHS-biotin. Solutions containing potential protein ligands of interest are injected over the sensor chip surface, and the binding is measured in real time (Femig, In: *Proteoglycan protocols*, Ed. R. V. Iozzo, Humana Press, Totowa, N.J., USA, 2001). Bacterially expressed recombinant human IL-13 (rhIL-13) readily binds to heparin immobilized by this method. Indeed, rhIL-13 bound best when the binding buffer was slightly acidic (pH 6), (FIG. 1) and this binding was specific as there is little interaction of rhIL-13 with sensor chips lacking heparin. Moreover, the binding of rhIL-13 to heparin is concentration dependent (FIGS. 1A and 1B).

Preparations of the anionic glycoconjugate, pentosan polysulfate (PPS) inhibit the binding of IL-13 to heparin immobilized on the BIACORE sensor chip. Titration experiments indicate that PPS is a better inhibitor of IL-13 binding to immobilized heparin than heparin itself. These data indicate that PPS is binding to the same site on IL-13 that heparin binds.

PPS is a sulfated xylan. Not all sulfated xylose polysaccharides bind IL-13, the size of the sulphated xylose polysaccharides is an important component of its ability to bind to IL-13 and thereby block IL-13 binding to heparin. Small sulfated xylans of degree of polymerization (D.P.) 4 or less were unable to inhibit IL-13 binding to immobilized heparin.

Example 4

Functional Analyses of Heparin on the Target Protein, IL-13

Heparin inhibited the proliferation of a human IL-13 responsive cell line. This occurs at very low doses and is not due to a toxic effect of the heparin because other, similarly sulfated polysaccharides, at the same concentrations of IL-13 and polysaccharide have no effect. These experiments utilize the TF-1.8 cells. TF-1.8 cells are a subclone of the TF-1 cells that have been selected for growth in IL-4, and because IL-4 and IL-13 share a receptor these cells are also responsive to IL-13. TF-1 cells were originally established from a bone marrow sample from a male with severe pancytopenia. These cells are dependent on IL-3 or GM-CSF for long term growth and are responsive to a variety of cytokines including IL-4 and IL-13.

TF-1.8 cells have been transfected with the firefly luciferase gene contained in the expression vector, pPGK-puromycin-luciferase (Coombe et al, *J. Immunol. Methods* 215:145-150, 1998). The positive transfectants are cloned to produce a line with good luciferase expression. The proliferation assays are carried out in 96-well microplates suitable for such assays (Falcon). The wells are flat bottomed, with white sides and a clear bottom. Cells are washed to remove any cytokine in the growth medium and then resuspended in RPMI/5% w/v FCS. The cells are counted with a Coulter Z2 Particle Counter and Size Analyzer (Coulter Electronics, England) and routinely $2.5\times10^4$ cells are added to microplate wells that contain either no IL-13 (negative control) or various dilutions of IL-13. When the effect of PPS, or other sulfated polysaccharides is to be measured, the wells also contain various concentrations of these molecules.

The cells proliferate for 48 hours at 37° C. in a humidified atmosphere, after which the luciferase activity is measured by the addition of 50 μl of luciferase substrate buffer (50 mM Tris-HCl, pH 7.8, 15 mM $MgSO_4$, 33.3 mM DTT, 0.1 niM EDTA, 0.5 mM Na-luciferin, 0.5 mM ATP, 0.25 mM lithium Co A and 0.5% v/v TRITON X-100). Immediately after the addition of the luciferase buffer the plate is assayed for luciferase activity. Light emissions are detected on a Victor 1420 Multilabel counter (Wallac, Turku, Finland).

Using this assay, the inventors demonstrated that heparin markedly inhibits the IL-13 dependent proliferation of TF-1.8 cells (FIGS. 2A and B) giving 75-80% inhibition of IL-13 mediated cell proliferation at concentrations of 5-10 μg/ml and 55-60% inhibition at the lower concentrations of 2.5-1.25 μg/ml. Heparin at 10 μg/ml was a very effective inhibitor of cell proliferation over a wide range of IL-13 concentrations (FIG. 2A). Moreover, sucrose octasulfate at a concentration of 10 μg/ml has very little inhibitory activity of IL-13 mediated cell proliferation even at low IL-13 concentrations (FIG. 2A).

The ability of fluorescent-labeled IL-13 to bind to its receptor, in the presence or absence of heparin, is examined.

These experiments are performed using different concentrations of IL-13, which has been conjugated with ALEX-AFLUOR-488 dye, and heparin. Comparisons with other sulfated polysaccharides shown not to have activity in inhibiting the IL-13 dependent proliferation of TF-1.8 cells, demonstrates specificity.

Example 5

Heparin and Heparan Sulfate Oligosaccharides Bind IL-13

HLGAGs may be partially digested by a number of means, including enzymatic digestion with heparinases and chemical digestion using agents such as nitrous acid, alkaline β-elimination and oxidation in conjunction with alkaline depolymerization (Conrad, Heparin binding proteins. Academic Press, San Diego, 1998). The enzymes heparinase I and heparinase III cleave at specific sites on the heparin/heparan sulfate chain: heparinase I at IdoA residues with N-sulfated glcN domains, and heparinase III at GlcA residues in unsulfated N-acetyl GlcN domains.

Heparan sulfates are depolymerized according to the procedures described by Turnbull et al. (*Proc. Natl. Acad. Sci. USA* 96(6): 2698-2703, 1999), Heparin was depolymerized in accordance with the procedure described by Chai et al. (*Anal. Chem.* 70(10): 2060-2066, 1998). Briefly, heparin (5 g) and albumin (4 mg) were dissolved in 50 ml 30 mM $CH_3CO_2Na$, containing 3 mM $CaCl_2$ and adjusted to pH 7 with 0.2 M $NaHCO_3$. Heparinase I, EC 4.2.2.7, (2 IU) was added and the mixture incubated at 30° C. for 16 hrs. The mixture was boiled for 3 minutes, aliquoted into small volumes (5 ml) and frozen. Aliquots were thawed, centrifuged and filtered before injection (1 ml) on the size-exclusion chromatography system.

SEC was performed on a two 90×1.5 cm glass columns connected in series. The first column was packed with P6 fine and the second with P 10 fine. The columns were eluted with 0.25 M NaCl at a flow rate of 0.25 ml/min using a Gilson model 307 titanium pump (Middleton, Wis., USA) and the effluent monitored with a Shimadzu RID-10 refractive index detector (Melbourne, Victoria, Australia). Data was acquired using Gilson Unipoint software. Fractions of 1 ml were collected. Fractions adjacent to the peak maxima were pooled, lyophilized and desalted on a fast desalting column. The desalted fragments were lyophilized, redissolved in water and stored at −20° C. The concentration of each fragment was determined spectrophotometrically at 232 nm in 30 mM HCl using the extinction coefficient of 5500 $mol^{-1}$ $cm^{-1}$. The size of the oligosaccharides were confirmed using MALDI MS (vide infra).

Figure 3:
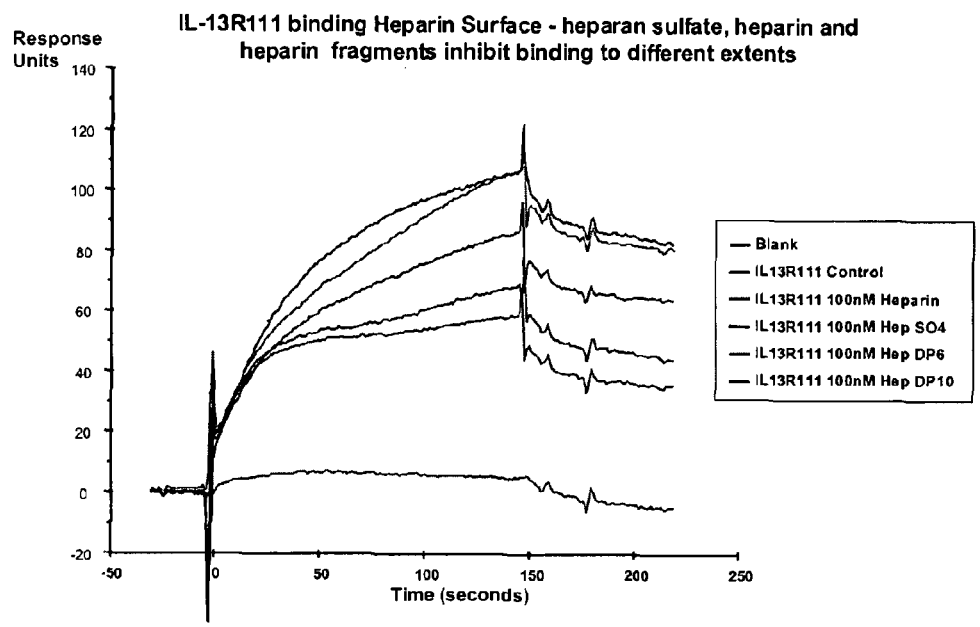
FIGS. 3A and B are graphical representations showing the ability of heparin and heparan sulfate fragments to bind to IL-13 and to inhibit IL-13 activity is dependent upon fragment size. (A) Graphical representation showing the bidnign of IL-13R111 to immobilized heparin on a BIACORE sensor chip as determined by surface Plasmon resonance. IL-13 (75 nM) was injected alone or following preincubation with heparin (100 nM), heparan sulfate (100 nM), heparin DP10 (100 nM) and heparin DP6 (100 nM). (B) Graphical representation of TF1 cell proliferation in the presence of various sizes of heparin (hep) and heparan sulfate (HS) fragments. The saccharides were tested at 1 µg/ml and 2.5 µg/ml.
Figure 3:
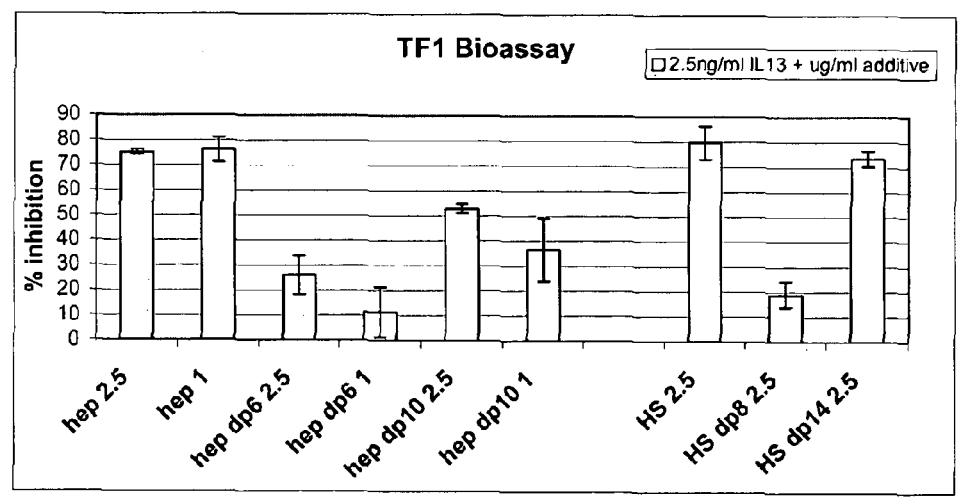

This library of heparin and heparan sulfate fragments of uniform saccharide number was then used in the BIACORE sensor chip assay to determine their ability to inhibit the binding of IL-13 to immobilized heparin. These experiments indicate that pools of heparin fragments of size DP 6 or less are too small for effective binding to IL-13 and thereby blocking IL-13 from binding to immobilized heparin. Heparin oligosaccharides DP 10 and larger were effective in this assay to varying degrees, but full length heparin or heparan sulfate were the most effective (FIG. 3A).

The library of heparin and heparan fragments of uniform saccharide number were also used in a TF-1 cell proliferation assay to determine whether all saccharides had the same ability to inhibit IL-13 stimulated cell proliferation. These experiments indicated that not all heparin or heparan sulfate oligosaccharides had the same ability to inhibit IL-13 activities. Small heparin fragments (DP6) had little effect whereas larger heparin fragments (DP10) were more effective (FIG. 3B). Similarly small heparan sulfate fragments (DP8) were ineffective inhibitors whereas larger fragments (DP14) were as effective in this assay as full length heparan sulfate (FIG. 3B).

Example 6

Functional Analyses of Pentosan Polysulfate on the Target Protein, IL-13

PPS inhibited the proliferation of a human IL-13 responsive cell line. This occurs at very low doses and is not due to a toxic effect of the pentosan polysulfate because other, similarly sulfated polysaccharides, at the same concentrations of IL-13 and polysaccharide have no effect. These experiments utilize the TF-1.8 cells. TF-1.8 cells have been transfected with the firefly luciferase gene contained in the expression vector, pPGK-puromycin-luciferase (Coombe et al, 1998 supra). The proliferation assays are carried out in 96-well microplates suitable for such assays (Falcon). The wells are flat bottomed, with white sides and a clear bottom. Cells are washed to remove any cytokine in the growth medium and then resuspended in RPMI/5% w/v FCS. The cells are counted with a Coulter Z2 Particle Counter and Size Analyzer (Coulter Electronics, England) and routinely 2.5× $10^4$ cells are added to microplate wells that contain either no IL-13 (negative control) or various dilutions of IL-13. When the effect of PPS is to be measured, the wells also contain various concentrations of this molecule.

The cells proliferate for 48 hours at 370 C in a humidified atmosphere, after which the luciferase activity is measured by the addition of 50 µl of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v TRITON X-100). Immediately after the addition of the luciferase buffer the plate is assayed for luciferase activity. Light emissions are detected on a Victor 1420 Multilabel counter (Wallac, Turku, Finland).

Using this assay, the inventors demonstrated that PPS markedly inhibits the IL-13 dependent proliferation of TF-1.8 cells (FIG. 2B) with 75-80% of IL-13 mediated cell proliferation blocked at PPS concentrations of 5-10 µg/ml.

Figure 4:
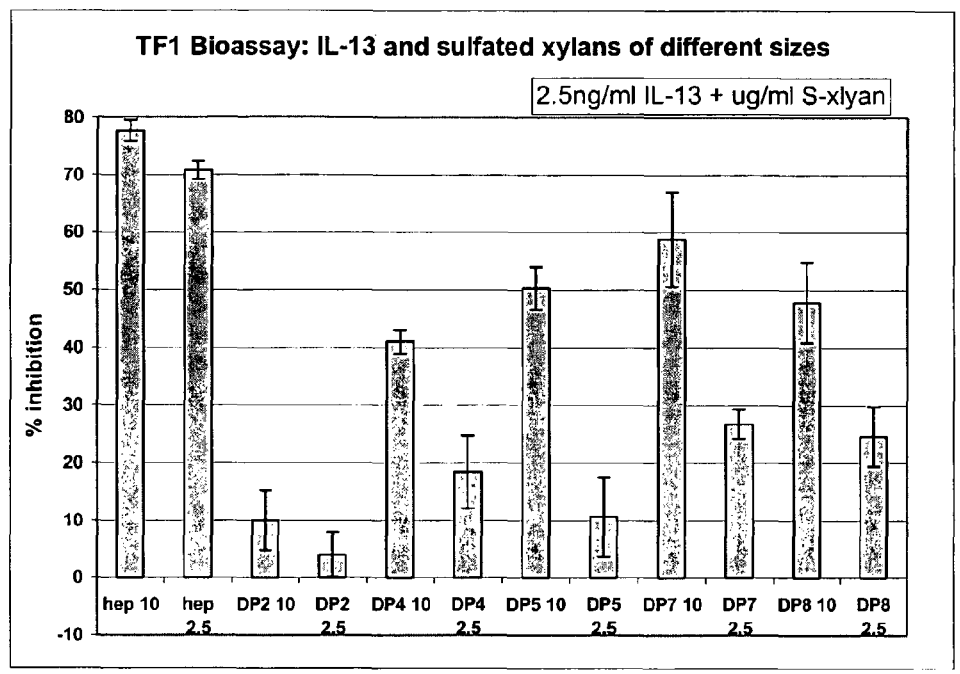
FIG. 4 is a graphical representation of showing the ability of sulfated-xylans of sizes DP2, DP4, DP5, DP7 and DP8 to block the IL-13 dependent proliferation of TF-1 cells. The different sized sulfated-xylans are used at 10 and 2.5 µg/ml and the IL-13 is at 2.5 ng/ml. The mean % inhibition+/- standard deviation of 3 replicates is shown.

The ability of sulfated xylans to inhibit IL-13 mediated cell proliferation is size dependent. These experiments utilized the TF-1 cell line from which the TF1.8 cells were derived. The assay is performed as described above with the TF1.8 cells the differences being the concentration of IL-13 required for cell growth and the fact that cell number is determined using a dye. Briefly, proliferation assays are carried out in 96-well microplates suitable for such assays. Cells are washed to remove any cytokine in the growth medium and then resuspended in RPMI/5% w/v FCS and routinely 2.5×$10^4$ cells are added to microplate wells that contain either no IL-13 (negative control) or various dilutions of IL-13. When the effect of the different sized sulfated xylans was measured, the wells also contained various concentrations of these molecules and the IL-13 concentration was held constant at 2.5 ng/ml. The cells proliferated for 48 hours, after which the number of cells present was quantified by staining with 204 per well of the AQUEOUS ONE dye for 3 hours and then absorbance was read at 490 nm. Smaller polysaccharides comprising 2 or 3 sulfated xylose units 1-4 linked were ineffective inhibitors when used at either 2.5 µg/ml or 105 µg/ml. The larger polysaccharides comprising 4, 5, 7, or 8 sulfated xylose units linked 1-4 inhibited IL-13 dependent TF-1 cell proliferation but the most effective were septa- and octa-saccharides and a mixture of sulfated xylose polysaccharides all larger than an octasaccharide. (FIG. 4 shows the data for the effect of sulfated-xylans of size DP2, DP4, DP5, DP7 and DP8 on the IL-13 dependent proliferation of TF-1 cells The ability of fluorescent-labeled IL-13 to bind to its receptor, in the presence or absence of PPS, is examined. These experiments are performed using different concentrations of IL-13, which has been conjugated with ALEX-AFLUOR-488 dye, and PPS. Comparisons with other sulfated polysaccharides shown not to have activity in inhibiting the IL-13 dependent proliferation of TF-1.8 cells, demonstrates specificity.

Example 7

Docking Protocol for Identification of Heparin Binding Sites on IL-13 Surfaces

The docking strategy developed identifies potential heparin binding sites on protein surfaces, for use both in the illustration and rationalization of experimental results such as NMR titrations or the design of site-directed mutagenesis experiments. As it is not necessarily the case that heparin structures will bind to proteins in a single, defined orientation, no emphasis is placed on the detailed prediction of the geometry of the complexes, or accurate calculation of the interaction energy. Rather than the conventional use of docking techniques, in which the geometry of a small ligand molecule in a known high-affinity binding site is optimized, protocol is used to screen the entire surface of a small protein for clusters of basic residues which offer suitable shape and charge profiles complementary to the pattern of acidic substituents along the heparin chain.

Docking of several heparin oligosaccharide ligand models to protein structures is performed as previously described (Forster and Mulloy, *Biochem. Soc. Trans.* 34:431, 2006) using Autodock, version 2.4 (Morris et al, *J. Comput. Aided Mol. Des.* 10:293, 1996), with partial charges for protein atoms taken from the AutoDock version of the AMBER force field. Co-ordinates for the heparin oligosaccharide ligands were derived from the NMR structure for the predominant repeating disaccharide of heparin lhpn.pdb (Mulloy et al, *Biochem. J.* 293:849, 1993) with partial atomic charges from ab initio calculations using the Jaguar program (Schrodinger Inc, Portland, Oreg., USA) on 1-OMe 4-OMe substituted monosaccharides. Two pentasaccharide ligands were used, each with glucosamine at both reducing and nonreducing termini. For one of these, the two iduronate residues were both in the $^1C_4$ conformation, and for the other they were both in the $^2S_0$ conformation; in heparin both these forms are in equilibrium. All the exocyclic bonds in these pentasaccharide models were regarded as rotatable with the exception of the glycosidic linkages. Some calculations were also performed using a completely rigid endecasaccharide ligand model.

Docking is typically performed on a grid of 120×120×120 points, with the addition of a central grid point. The grid was centred on the mean of the coordinates of the protein. Grid spacing was 0.7 Angstroms, leading to a grid of 84×84×84 Angstroms. This determines the largest protein that can be studied by this protocol. Separate grids of VDW interaction energy are then calculated for each atom type in the ligand (C, N, H, S, O) and an electrostatic interaction energy grid is computed for a single electron charge. These grids are used during the docking process to rapidly calculate the interaction energy of the ligand with the protein. This is achieved by finding the grid points surrounding each ligand atom and using an interpolation procedure to find the energy contribution at the current coordinates. The energies are then summed over all atoms in the ligand and the torsion energy terms added to the VDW and electrostatic energies. During the docking procedure the position, orientation and allowed torsion angles of the ligand structure are optimized by a monte carlo simulated annealing procedure. Initial simulation temperature (defined in RT units) of 1000 was used and a temperature reduction factor of 0.95 per cycle was used; typically 128 runs of 300 cycles were performed.

These parameters were selected in a validation study of the protocol, by performing simulations on a protein/heparin oligosaccharide complex of known crystal structure, that of FGF2 with a heparin hexasaccharide (1bfc.pdb) [Mulloy and Forster, *Glycobiology* 10:1147, 2000], adjusting parameters to most reliably reproduce the known heparin binding site. Docking is performed with a unit dielectric rather than a distant dependent dielectric as this was found more reliable in reproducing known binding sites. Docking calculations typically required approximately 50 minutes on a 300 MHz SGI octane workstation. Docked ligand coordinates are extracted from output files using a set of in-house PERL scripts.

Example 8

Use of Docking Calculations to Screen the Structure Database for Heparin-Binding Proteins The docking protocol is readily be performed on a medium-high throughput basis, so that the possibility arises of a systematic survey of proteins with known three-dimensional structures, in order to supplement the limited number of experimentally determined heparin-protein complexes (Imberty et al, Carbohydr. Res. 342:430, 2007). There are over 41,000 structures in the PDB, however, so an initial survey of a subset of solved protein structures is desirable. In the SCOP (Structural Classification of Proteins) [Murzin et al, J. Mol. Biol 247:536, 1995] system (available on the internet at: scop.mrclmb.cam.ac.uk/scop/), members of the Superfamily of 4-helical cytokines (in the Class of all-alpha proteins) including IL-13 form a suitable group. They are small proteins, related in functional terms as well as by structure, and all performing their biological functions outside the cell, so that their environment is rich in glycosaminoglycans.

Semi-automated docking calculations are performed using the program Autodock, as previously described (Forster and Mulloy 2006, supra), with co-ordinates for the heparin-based oligosaccharide ligands taken from the PDB file lhpn.pdb (Mulloy et al 1993, supra) and co-ordinates for human IL-13 derived from PDB files (available on the World Wide Web at: rcsb.org/pdb/) PDB ID: 1ijz. Only the structure of human IL-13 cytokines were chosen. Heparin-protein complexes calculated to have intermolecular interaction energies of less than—1000 kcal/mol are regarded as predictions of capacity to bind heparin; those with interaction energies of more than 0 were regarded as predicting no capacity to bind heparin. The energy units of the Autodock function are usually given as kcal/mol; the high figures in the Tables are a consequence of the high weighting given to electrostatic terms in the forcefield by using a unit dielectric constant. Values given should be understood as the results of a ranking function with no significance in absolute terms.

Co-ordinates are visualized and figures prepared using the programs Insight II and Weblab Viewer (Accelrys).

The binding properties of heparin pentasaccharides interacting with human IL-13 are listed in Table 3.

TABLE 3

Prediction of heparin binding to IL-13

| Cytokine (abbreviation) | PDB filename | Intermolecular Interaction Energies for pentasaccharide ligands | | Position of heparin binding site[2] |
|---|---|---|---|---|
| | | $IdoA^1C_4$ | $IdoA^2So$ | |
| Interleukin-13 | 1ijz.pdb (monomer) | −1099 | −1120 | AB loop (K25) and Helix D (K97, K104, K105, R108) |

Figure 5:
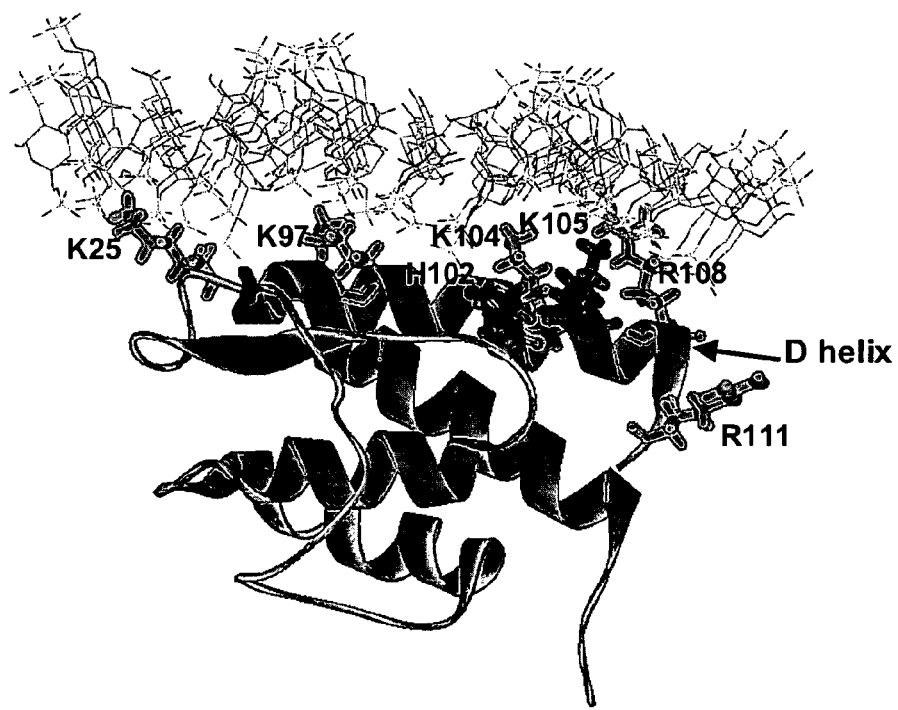
FIG. 5 is a representation showing the location of amino acids that affect human IL-13 WTbinding to GAGs or polyanioinc glycoconjugates. (A) Molecular modeling of the interaction of a rigid heparin endecasaccharide with the key IL-13 amino acids being represented as sticks. Ten different docking orientations of the heparin fragment are shown. The heparin chains are displayed as a line colored by element whereas the protein is displayed as a ribbon.

Docking was also performed using a completely rigid heparin endecasaccharide and the results of this analysis are illustrated in FIG. 5.

Example 9

Determination of the Heparin Binding Site on IL-13

FIG. 1 shows the BIACORE sensor chip binding curves of wild-type IL-13 binding to heparin immobilized on a biosensor chip. A number of different concentrations of IL-13 are shown.

Figure 6:
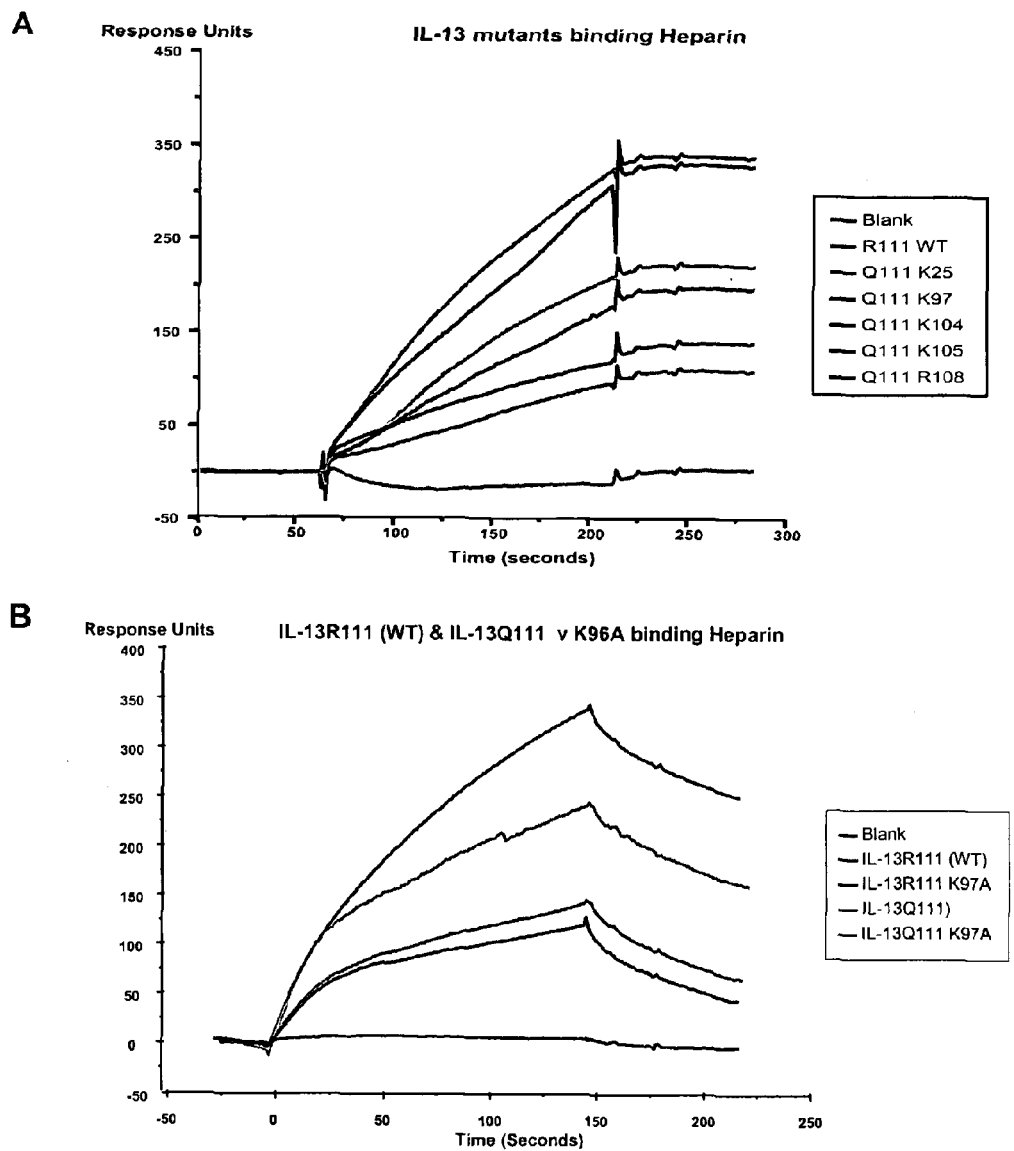
FIG. 6 is a graphical representation of the binding of various IL-13 mutants to immobilized heparin. Heparin was immobilized on a BIACORE sensor surface and the various IL-13 molecules (75 ngm in BisTris pH 6.00, 0.15M NaCl 0.005% Tween 20) were passed over the surface in the fluid phase The blank is a buffer alone passed over a surface without coupled heparin. (A) The binding of wild type IL-13 with arginine in the 111 position (R111 WT) is compared to IL-13 mutants where a glutamine is at the 111 position, to represent the naturally occurring polymorphism of 20% of the Caucasian population, and a second mutation on the Q111 background where the following amino acids have been converted to alanine: K25, K97, K104, K105 and R108. (B) The binding to immobilized heparin of wild type IL-13 with arginine in the 111 position (IL-13R111) is compared to wild type IL-13 where lysine at position 97 has been mutated to alanine (IL-13R111 K97A); IL-13 with glutamine at position 111 (IL-13 Q111), and IL-13 with glutamine at position 111 and the lysine at position 97 has been mutated to alanine (IL-13Q111 K97A).
Figure 7:
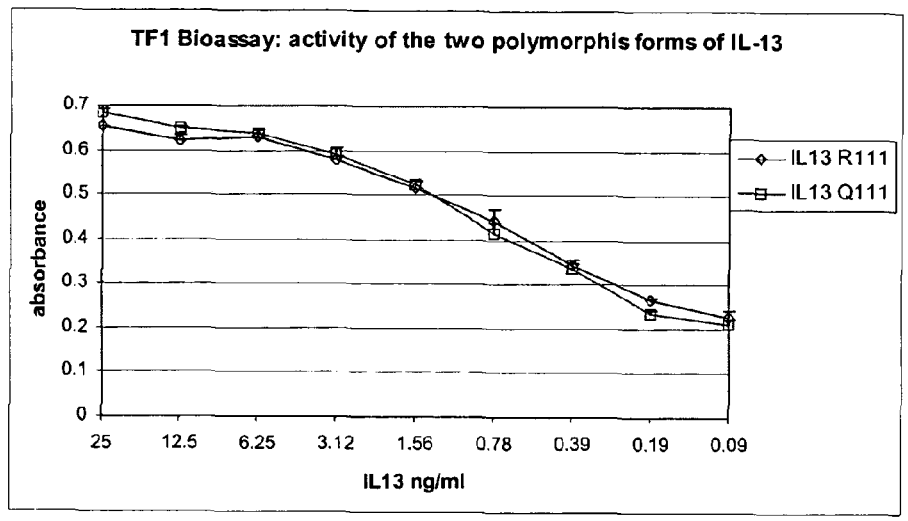
FIG. 7 is a graphical representation of the biological activity of the two polymorphic forms of human IL-13, IL-13 with arginine at position 111 and IL-13 with glutamine at position 111. The biological activity is measured as the IL-13 induced proliferation of TF-1 cells. (A) The IL-13 dependent proliferation of TF-1 cells is identical regardless of what polymorphic form is assayed. (B) Heparin is very effective at inhibiting the biological activity of both forms of IL-13.
Figure 7:
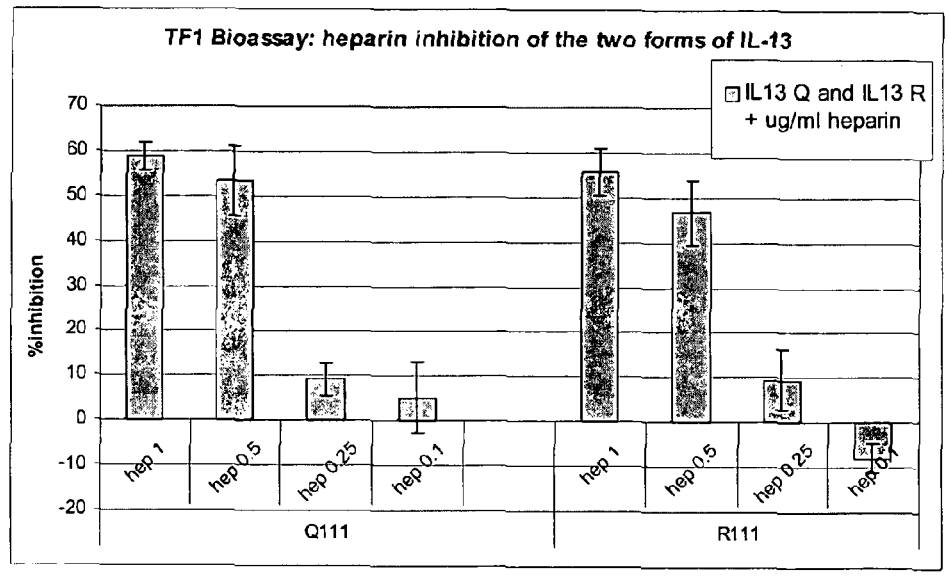
Figure 8:
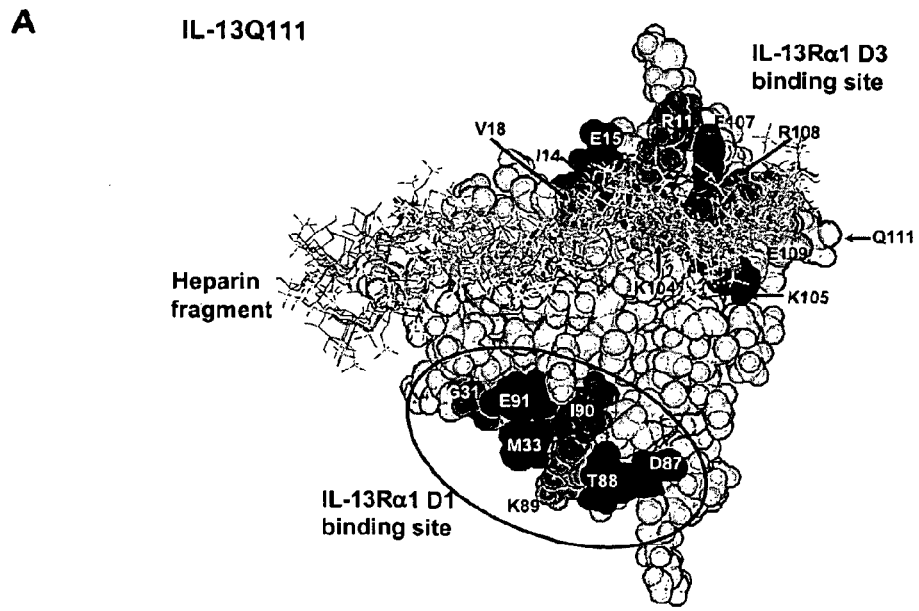
FIGS. 8A and B are diagrammatic representations of space filed models of Il-13. Heparin fragments bind to both naturally occurring forms of IL-13 at the same location and in both cases heparin binding partially masks the site on IL-3 that is recognized by domain 3 of IL-13Rα1. (A) Space filled model of human IL-13Q111 binding a heparin llmer. (B) Space filled model of human IL-13R111 (wild-type) binding a heparin 11 mer. The amino acids involved in binding the domains 1 and 3 of IL-13Rα1 are shown. Amino acids in the D helix are shown in various shades of green whereas those in the A helix are in various shades of red and orange. The heparin fragments are shown as lines colored by element. Ten different docking orientations are shown.
Figure 8:
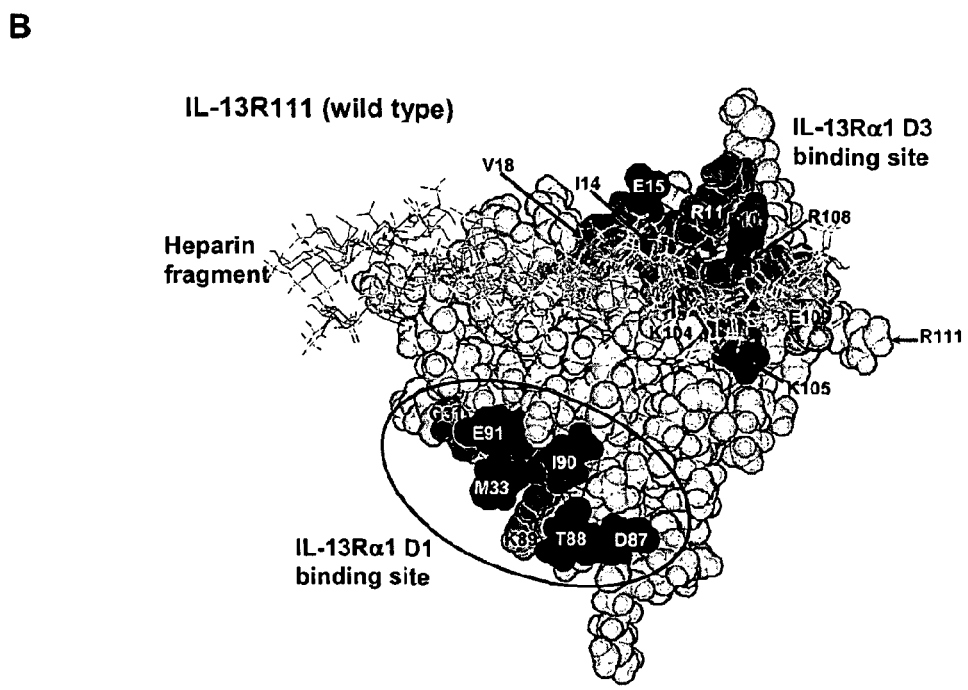

Site directed mutagenesis was performed on IL-13. Basic residues and some acidic residues within the proposed heparin binding site were changed to alanine (A) and the proteins expressed using the baculovirus expression system. Insect cell expressed proteins were purified on either a monoclonal anti IL-13 antibody affinity column or a polyclonal anti-IL-13 antibody affinity column and checked for purity by SDS-PAGE and silver staining. Mutant IL-13 proteins were examined for their ability to bind heparin immobilized on a biosensor chip and binding was assessed using a BIACORE 2000 sensor chip. Binding curves for wild type IL-13 and some of the mutant proteins are shown in FIG. 6. These data indicate that amino acid residue numbers K25 in the AB loop and K97, H102, K104, K105, R108, and R111 are key residues in the heparin binding site on wild type IL-13. The orientation of these critical amino acids in IL-13 for heparin binding are shown in FIG. 5. More particularly these data indicate that heparin binds to both of the common forms of IL-13, the wild type where arginine is in the 111 position and the polymorphic form where glutamine is in position 111 (IL-13Q111), although wild type IL-13 binds heparin more strongly. From the molecular modeling it appears that R111 does not directly interact with the heparin chain but it does contribute to the overall basic charge of the C-terminal region of the D helix and because of this heparin binds the R111 form of IL-13 more effectively (FIG. 5 and FIG. 6).

To obtain an indication as to the ability of heparin to bind the various IL-13 mutants in solution the ability of soluble heparin to bind the various IL-13 mutants and so block the interaction of the mutants with immobilized heparin was determined. Heparin was immobilized on a BIACORE biosensor chip surface and the IL-13 mutants plus various concentrations of soluble heparin were in the fluid phase. The concentration of heparin required to inhibit the IL-13 proteins binding by 50% ($IC_{50}$) were determined and these data are shown in Table 4.

TABLE 4

Ability of soluble heparin to inhibit IL-13 proteins from binding to immobilized heparin

| | $IC_{50}$ nM | |
|---|---|---|
| IL-13 protein | End point heparin* | Low density heparin* |
| IL-13 WT (R111) | 25 | 3 |
| IL-13Q111 K25A | 50 | 4.5 |
| IL-13Q111 K97A | 50 | 8 |
| IL-13Q111 H102A | 30 | 4.5 |
| IL-13Q111 K104A | 50 | 8 |

*Two differently prepared biosensor surfaces were used. The end point heparin surface was coupled with heparin biotinylated at the reducing terminus. The low density surface was prepared with heparin biotinylated along the GAG chain. These biotinylation methods and methods of coupling heparin to biosensor surfaces are described in Osmond et al, *Analyt. Biochem.* 310: 199-207, 2002.

Molecular modeling calculations of the interaction energies are in general accordance with the experimental data. These calculations have been performed for mutations on both backgrounds of IL-13: the Q111 form and the R111 form, and heparin fragments comprising 11 saccharides and 5 saccharides have been modeled. In addition the heparin pentamer has been modeled in the $^1C_4$ chair and the $^2S_0$ skew-boat conformation of the iduronic acids and the free energies of interaction have been calculated for each. These data are given in Table 5 and Table 6. In all cases the interaction is stronger for the longer heparin fragment compared to the heparin pentamer regardless of the iduronic conformation.

TABLE 5

Interaction energies of the docked heparin oligosaccharides binding to human IL-13: IL-13Q111 background*

| IL-13 protein* | Heparin 11-mer | 5-mer $^1C_4$ | 5-mer $^2S_0$ |
|---|---|---|---|
| 1IJZ | −1734 | −1099 | −1120 |
| IL-13Q111 | −1441 | −889 | −912 |
| K104A | −861 | −613 | −572 |
| K105A | −947 | −625 | −608 |
| K25A | −1038 | −810 | −810 |
| R108A | −882 | −595 | −606 |
| H102A | −1441 | −927 | −923 |
| K97A | −923 | −716 | −728 |

*Starting co-ordinates: 1IJZ.pdb, IL-13 monomer, 111R variant 111q variant and listed mutants built by residue replacement in Insight, no further minimization as all the basic residues were fully exposed, except possibly for H102

TABLE 6

Interaction energies of the docked heparin oligosaccharides binding to human IL-13: IL-13R111 background*

| IL-13 protein* | Heparin 11-mer | 5-mer $^1C_4$ | 5-mer $^2S_0$ |
|---|---|---|---|
| 1IJZ | −1734 | −1099 | −1120 |
| K104A | −1121 | −701 | −706 |
| K105A | −1207 | −759 | −756 |
| K25A | −1386 | −998 | −1014 |
| R108A | −1184 | −694 | −685 |
| H102A | −1729 | −1098 | −1125 |
| K97A | −1273 | −932 | −928 |

*Starting co-ordinates: 1IJZ.pdb, IL-13 monomer, 111R variant Listed mutants built by residue replacement in Insight, no further minimization as all the basic residues were fully exposed, except possibly for H102

Example 10

Figure 2:
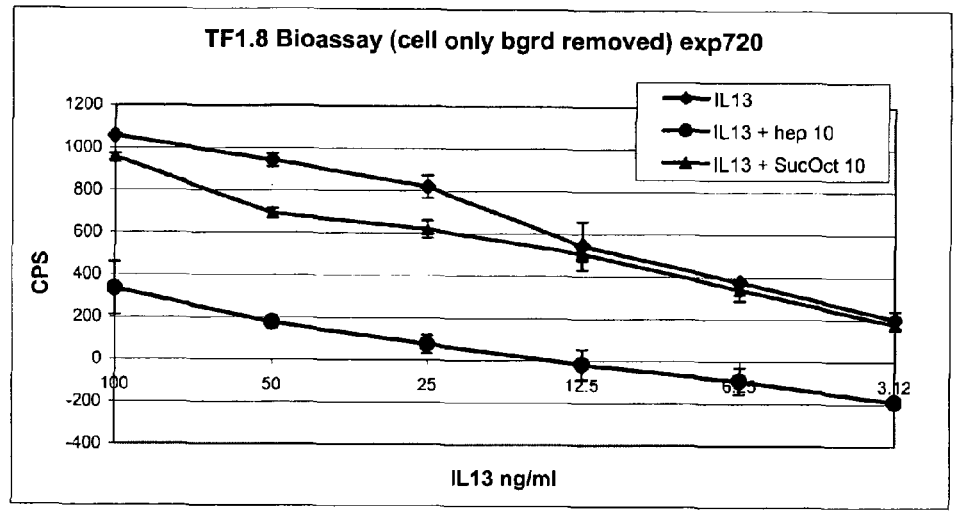
FIGS. 2A and B are graphical representations showing the ability of various anionic polysaccharides to block the cell proliferation activity of IL-13. (A) the effect of heparin or sucrose octasulfate (both at 10 µg/ml) on the IL-13 mediated cell proliferation of TF1.8 cells; a titration of IL-13 is shown. (B) is a graphical representation showing the dose-response curves of pentosan (dashed line) and heparin (full line) for IL-13 dependent proliferation of TF1.8 cells at 25 ng/ml of IL-13.
Figure 2:
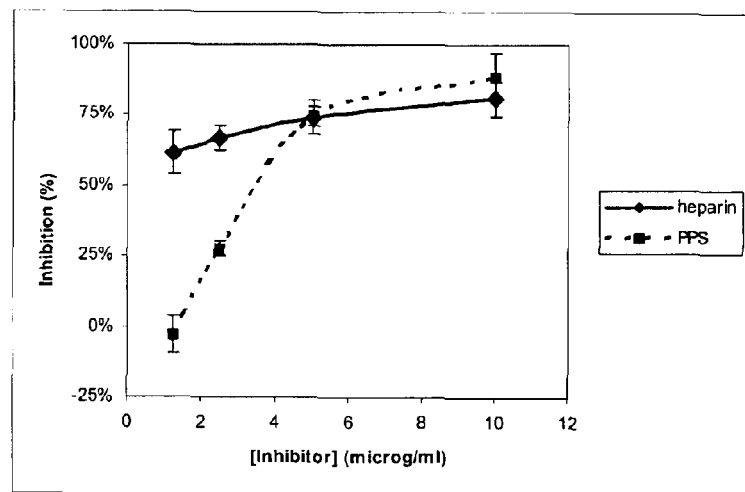

The Site of Heparin Binding to the IL-13 Proteins Overlaps with the Receptor Binding Sites It was demonstrated in FIG. 2 and FIG. 4 that heparin could inhibit the proliferation of TF1.8 cells and TF-1 cells. A key part of the main heparin binding site on IL-13 is on helix D and is centred around the basic amino acids K97, H102, K014, K105 and R108. Amino acids in the D-helix have also been described as important for binding to IL-13Rα1 and/or IL-13Rα2, these are 11102, K104, K105, R108, E109 and R111 (Arima et al, 2005 supra; Madhankumar et al, 2002 supra). These data are supported by molecular modeling studies and the crystal structures of the signaling complex of IL-4Rα/IL-13/IL-13Rα1. Analyses of the crystal structure further suggest K104 and R108 on IL-13 are critically important for the interactions with IL-13Rα1 domain 3 (LaPorte et al, 2008 supra). A stripe of amino acids on the A and D helices demarcates a hydrophobic canyon lined by the alkyl moieties of these amino acids. These side chains form clefts into which the receptors insert to contact the main chains of the cytokine A and D helices and of particular importance are the side chains of amino acids R108 and K104 on the D helix. Whereas it appears that R111 is important for binding to the soluble receptor IL-13Rα2 (Andrews et al, 2007 supra). Domain 1 of IL-13Rα1 interacts with a hydrophobic saucer-shaped patch formed by the alkyl side chains of M33, D87, K89, T35 (LaPorte et al, 2008 supra).

The concentration of each of the IL-13 mutants required to produce 50% of the maximal TF-1 cell proliferation was determined and these data are given in Table 7. The IL-13R111 wild type and the IL-13Q111 variant are shown for comparison.

TABLE 7

Concentration of IL-13 required for 50% TF-1 cell proliferation

| IL-13 proteins | ED50 ng/ml ave | ED50 ng/ml stdev |
|---|---|---|
| R111 wt | 1.2 | 0.58 |
| Q111 | 1.26 | 0.51 |
| (Q)H102A | 5.31 | 0.83 |
| (Q)K104A | 46.22 | 12.2 |
| (Q)K105A | 22.63 | 2.4 |
| (Q)R108A | 3.2 | 0.65 |
| (Q)K97A | 1.33 | 0.38 |
| (Q) K25A | 2.64 | 0.48 |

The data in Table 7 agree with that published indicating the prime role of amino acids on the C-terminal end of the D helix for IL-13 function.

The cell proliferative activity of both the main polymorphic forms of IL-13: IL-13Q111 and IL-13R111 are comparable in the TF-1 cell assay and both are equally sensitive to inhibition by heparin FIGS. 7A and B. The TF-1 cell proliferation assay was used to obtain these data. Details of the assay are given in Example 6. This clearly indicates that heparin or a heparin fragment or a polyanionic polysaccharide, or a polyanionic glycoconjugate can effectively inhibit the biological activity of both the naturally occurring forms of IL-13.

Molecular modeling of heparin fragments binding to IL-13Q111 and IL-13R111 reveals that the heparin fragments bind to IL-13 at a site that overlaps that recognized by domain 3 of IL-13Rα1. The heparin chains bind to both IL-13Q111 and IL-13R111 with approximately the same orientation (FIG. 8). This means that the mechanism for inhibiting the biological activity of the two forms of IL-13 are identical.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Alban and Franz, *Biomacromolecules* 2:354, 2001
Altschul et al, *Nucleic Acids Research* 25:3389-3402, 1997
Andrews et al, *J. Immunol.* 176:7456-7461, 2006
Andrews et al, *J. Allergy Clin Immunol.* 120:91-97, 2007
Arima et al, *J. Biol. Chem.* 280:24915-24922, 2005
Boeckmann et al, *Nucleic Acids Research* 31:365-370, 2003
Bryson et al, *Nucleic Acid Research* 33:W36-38, 2005
Burns et al, *Physiol Rev* 83:309-336, 2003\
Caldwell et al, *Int J Biochem Cell Biol* 28(2):203-216, 1996
Cardin and Weintraub, *Arteriosclerosis* 9(1):21-32, 1989
Chai et al. *Anal. Chem.* 70(10): 2060-2066, 1998
Conrad, Heparin binding proteins. Academic Press, San Diego, 1998
Coombe et al, *J. Immunol. Methods* 215:145-150, 1998
de Waal Malefyt and de Vries, *The Cytokine Handbook,* 3rd *Edn*. A. W. Thomson, Editor: 427-442, 1998
Douguet and Labesse, *Bioinformatics* 17:752-753, 2001
Dubreuil et al, *Tetrahedron* 55: 7573-7582, 1999
Eisenmesser et al, *J. Mol. Biol.* 310:231-241, 2001
Fabbri et al, *Inflamm Res* 48:239-246, 1999
Fernig, In *Proteoglycan Protocols*, Ed. R. V. Lozzo, Human Press, Totowa, N.J. USA, 2001
Fiser et al, *Protein Sci* 9(9):1753-1773, 2000
Forster and Mulloy, *Biochem Soc Trans* 34(3):431-434, 2006
Fromm et al, *Arch Biochem Biphys* 343(1):92-100, 1997
Gilson and Honig, *Nature* 330(6143):84-86, 1987
Hetenyi and van der Spoel, *Protein Sci* 11(7):1729-1737, 2002
Hileman et al, *Bioessays* 20(2):156-167, 1998
Imberty et al, *Carbohydr. Res.* 342:430, 2007
Kelley et al, *J Mol Biol* 299(2):499-520, 2000
Kreuger and Spillmann, *J Cell Biol* 174:323, 2006
LaPorte et al, *Cell* 132:259-272, 2008
Laskowski et al, *Journal of Applied Crystallography* 26(2): 283-291, 1993
Madhankumar et al, *J. Biol. Chem.* 277:43194-43205, 2002
Margalit et al, *J Biol Chem* 268(26):156-167, 1993
Mehler and Somajer, *Protein Eng* 4(8):903-910, 1991
Mohammadi et al, *Curr. Opin. Struct. Biol.* 15:506, 2005
Morris et al, *J. Comput. Aided Mol. Des.* 10:293, 1996
Morris et al, *Journal of Computational Chemistry* 19(14): 1639-1662, 1998
Moy et al, *J. Mol. Biol.* 310:219-230, 2001
Mulloy and Forster, *Glycobiology* 10:1147, 2000
Mulloy et al, *Biochem J* 293(3):849-858, 1993
Mulloy, *Anais Acad. Bras. Cienc.* 77:651, 2005
Murzin et al, *J. Mol. Biol.* 247:536, 1995
Oshima and Puri, *J. Biol. Chem.* 276:15195-15191, 2001
Osmond et al, *Analyt. Biochem.* 310:199-207, 2002

Ostrovsky et al, *J. Biol. Chem.* 277:2444, 2002
Pearson and Lipman, *PNAS* 85(8):2444-2448, 1988
Petitou and van Boeckel, *Angew. Chem. Int. Edit* 43:3118, 2004
Raghuraman et al, *J Med Chem* 49(12):3553-3562, 2006
Rost et al, *Nucleic Acid Research* 32:W321-326, 2004
SalI and Blundell, *J Mol Biol* 234(3):779-815, 1993
Sanner and Python, *J Mol Graph Model* 17(1):57-61, 1999
Schneidman-Duhovny et al, *Proteins* 52(1):107-112, 2003
Schneidman-Duhovny et al, *Nucleic Acids Res* 33:W363-367, 2005
Shao et al, *J Biol Chem* 281(42):31689-31695, 2006
Smith, *Microcirculation* 7:385-394, 2000
Stauber et al, *Proc. Natl. Acad. Sci. USA* 97:49, 2000
Thompson and Debinski, *J. Biol. Chem.* 274:29944-29950, 1999
Thompson et al, *Nucleic Acids Research* 22:4673-4680, 1994
Tsiang et al, *J. Biol. Chem.* 270:16854-16863, 1995
Turnbull et al. *Proc. Natl. Acad. Sci. USA* 96(6): 2698-2703, 1999
Vieira de Almeida et al, *Tetrahedron* 55: 7251-7270, 1999
Weiner et al, *J. Am. Chem. Soc.* 106(3):765-784, 1984
Wills-Karp, *Immunol. Rev.* 202:175-190, 2004
Wynn, *Annu. Rev. Immunol.* 21:425-56, 2003
Zuegg et al, *Immunol. Cell Biol.* 79:332-339, 2001
Zurawski and dVries, *Immunol Today* 15:19-26, 1994

What is claimed is:

1. A method of identifying a polyanionic glycoconjugate as effective for treatment of an inflammatory process in a subject, said method comprising:
   determining whether said polyanionic glycoconjugate interacts with a polyanionic glycoconjugate-binding site on human interleukin 13 (IL-13), wherein the polyanionic glycoconjugate-binding site is a three-dimensional binding site defined by
   a conformation of amino acid residues comprising Q22, Q24 and K25 in the AB loop and a conformation of amino acid residues comprising K97, D98, H102, K104, K105, R108, E109 and R111 on one face of helix D of human mature IL-13; and
   identifying said polyanionic glycoconjugate as effective for said treatment if it interacts with said binding site.

2. The method of claim 1, wherein the polyanionic glycoconjugate identified as interacting with said polyanionic glycoconjugate-binding site on human IL-13 is a glycosaminoglycan (GAG).

3. The method of claim 1 wherein the inflammatory process is selected from the group consisting of inflammation, fibrosis, chronic graft rejection, stem cell differentiation and stem cell proliferation.

4. The method of claim 1 wherein the inflammatory process is allergic inflammatory disease.

5. The method of claim 4 wherein the allergic inflammatory disease is selected from the group consisting of asthma, allergic rhinitis, chronic obstructive pulmonary disease (COPD) and acute respiratory distress syndrome (ARDS).

* * * * *